United States Patent
Aghassian et al.

(10) Patent No.: US 10,632,319 B2
(45) Date of Patent: *Apr. 28, 2020

(54) EXTERNAL CHARGER FOR AN IMPLANTABLE MEDICAL DEVICE FOR DETERMINING POSITION USING PHASE ANGLE OR A PLURALITY OF PARAMETERS AS DETERMINED FROM AT LEAST ONE SENSE COIL

(71) Applicant: Boston Scientific Neuromodulation Corporation, Valencia, CA (US)

(72) Inventors: Daniel Aghassian, Glendale, CA (US); Thomas W. Stouffer, Chatsworth, CA (US); Jonathan Larcom, South Pasadena, CA (US); Gaurav Gupta, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/443,613

(22) Filed: Jun. 17, 2019

(65) Prior Publication Data
US 2019/0299013 A1 Oct. 3, 2019

Related U.S. Application Data

(63) Continuation of application No. 15/616,543, filed on Jun. 7, 2017, now Pat. No. 10,363,426.
(Continued)

(51) Int. Cl.
*H01M 10/46* (2006.01)
*A61N 1/378* (2006.01)
(Continued)

(52) U.S. Cl.
CPC ....... *A61N 1/3787* (2013.01); *A61N 1/36125* (2013.01); *A61N 1/36142* (2013.01);
(Continued)

(58) Field of Classification Search
CPC .. H02J 7/025; H02J 5/005; H02J 7/355; H02J 7/0042; H02J 50/90
(Continued)

(56) References Cited

U.S. PATENT DOCUMENTS 4,550,731 A 11/1985 Batina et al.
5,314,453 A 5/1994 Jeutter
(Continued)

FOREIGN PATENT DOCUMENTS

DE 19909479 8/2000
DE 10046027 3/2002
(Continued)

OTHER PUBLICATIONS

US 9,601,939 B2, 03/2017, Cong et al. (withdrawn)
(Continued)

*Primary Examiner* — Edward Tso
(74) *Attorney, Agent, or Firm* — Lewis & Reese, PLLC

(57) ABSTRACT

A charging system for an Implantable Medical Device (IMD) is disclosed having a charging coil and one or more sense coils preferably housed in a charging coil assembly coupled to an electronics module by a cable. The charging coil is preferably a wire winding, while the sense coils are preferably formed in one or more traces of a circuit board. One or more voltages induced on the one or more sense coils can be used to determine a phase angle between the voltage and a driving signal for the charging coil. The determined phase angle can then be used to determine the position of the charging coil relative to the IMD. Additionally, more than one parameter (phase angle, magnitude, resonant frequency)
(Continued)

may be determined using the voltage may be used to determine position, including the radial offset and depth of the charging coil relative to the IMD.

17 Claims, 22 Drawing Sheets

Related U.S. Application Data

(60) Provisional application No. 62/350,565, filed on Jun. 15, 2016.

(51) Int. Cl.
| | |
|---|---|
| *H02J 50/80* | (2016.01) |
| *H02J 50/12* | (2016.01) |
| *A61N 1/36* | (2006.01) |
| *A61N 1/372* | (2006.01) |
| *H01F 27/28* | (2006.01) |
| *H01F 38/14* | (2006.01) |
| *H02J 7/02* | (2016.01) |
| *A61N 1/05* | (2006.01) |

(52) U.S. Cl.
CPC ..... *A61N 1/37229* (2013.01); *H01F 27/2804* (2013.01); *H01F 27/2823* (2013.01); *H01F 38/14* (2013.01); *H02J 7/025* (2013.01); *H02J 7/027* (2013.01); *H02J 50/12* (2016.02); *H02J 50/80* (2016.02); *A61N 1/0534* (2013.01); *A61N 1/0551* (2013.01)

(58) Field of Classification Search
USPC .................................. 320/107, 108, 114, 115
See application file for complete search history.

(56) References Cited

U.S. PATENT DOCUMENTS

| | | |
|---|---|---|
| 5,591,217 A | 1/1997 | Barreras |
| 5,690,693 A | 11/1997 | Wang et al. |
| 5,704,352 A | 1/1998 | Tremblay et al. |
| 5,735,887 A | 4/1998 | Barreras, Sr. et al. |
| 5,749,909 A | 5/1998 | Schroeppel et al. |
| 5,769,877 A | 6/1998 | Barreras, Sr. |
| 5,807,397 A | 9/1998 | Barreras |
| 5,948,006 A | 9/1999 | Mann |
| 5,973,611 A | 10/1999 | Kulha et al. |
| 5,991,665 A | 11/1999 | Wang et al. |
| 6,009,878 A | 1/2000 | Weijand et al. |
| 6,047,214 A | 4/2000 | Mueller et al. |
| 6,058,330 A | 5/2000 | Borza |
| 6,088,619 A | 7/2000 | Hein et al. |
| 6,138,681 A | 10/2000 | Chen et al. |
| 6,212,430 B1 | 4/2001 | Kung |
| 6,275,737 B1 | 8/2001 | Mann |
| 6,298,271 B1 | 10/2001 | Weijand |
| 6,305,381 B1 | 10/2001 | Weijand et al. |
| 6,430,444 B1 | 8/2002 | Borza |
| 6,510,345 B1 | 1/2003 | Van Bentem |
| 6,516,227 B1 | 2/2003 | Meadows et al. |
| 6,553,263 B1 | 4/2003 | Meadows et al. |
| 7,167,756 B1 | 1/2007 | Torgerson et al. |
| 7,177,690 B2 | 2/2007 | Woods et al. |
| 7,177,698 B2 | 2/2007 | Klosterman et al. |
| 7,191,013 B1 | 3/2007 | Miranda et al. |
| 7,225,032 B2 | 5/2007 | Schmeling et al. |
| 7,286,880 B2 | 10/2007 | Olson et al. |
| 7,505,816 B2 | 3/2009 | Schmeling et al. |
| 7,650,192 B2 | 1/2010 | Wahlstrand |
| 7,774,069 B2 | 8/2010 | Olson et al. |
| 7,818,068 B2 | 10/2010 | Meadows et al. |
| 7,932,696 B2 | 4/2011 | Peterson |
| 8,005,547 B2 | 8/2011 | Forsberg et al. |
| 8,140,168 B2 | 3/2012 | Olson et al. |
| 8,169,185 B2 | 5/2012 | Partovi et al. |
| 8,214,042 B2 | 7/2012 | Ozawa et al. |
| 8,229,567 B2 | 7/2012 | Phillips et al. |
| 8,260,432 B2 | 9/2012 | DiGiore et al. |
| 8,311,638 B2 | 11/2012 | Aghassian |
| 8,321,027 B2 | 11/2012 | Mozzi et al. |
| 8,321,029 B2 | 11/2012 | Aghassian |
| 8,335,569 B2 | 12/2012 | Aghassian |
| 8,346,361 B2 | 1/2013 | Bauhahn et al. |
| 8,362,742 B2 | 1/2013 | Kallmyer |
| 8,401,663 B2 | 3/2013 | Aghassian |
| 8,401,664 B2 | 3/2013 | Chow et al. |
| 8,452,412 B2 | 5/2013 | Ibrahim |
| 8,473,066 B2 | 6/2013 | Aghassian et al. |
| 8,498,716 B2 | 7/2013 | Chen et al. |
| 8,509,912 B2 | 8/2013 | Morgan et al. |
| 8,554,322 B2 | 10/2013 | Olson et al. |
| 8,608,635 B2 | 12/2013 | Yomtov et al. |
| 8,612,013 B2 | 12/2013 | Forsell |
| 8,626,297 B2 | 1/2014 | Jaax et al. |
| 8,666,491 B2 | 3/2014 | Chen et al. |
| 8,682,444 B2 | 3/2014 | Aghassian et al. |
| 8,700,175 B2 | 4/2014 | Fell |
| 8,712,541 B2 | 4/2014 | Olson et al. |
| 8,744,592 B2 | 6/2014 | Carbunaru et al. |
| 8,751,001 B2 | 6/2014 | Grevious et al. |
| 8,831,730 B2 | 9/2014 | Mashiach et al. |
| 8,886,333 B2 | 11/2014 | Lui et al. |
| 8,901,878 B2 | 12/2014 | Prutchi et al. |
| 8,942,935 B2 | 1/2015 | Michaels et al. |
| 9,002,445 B2 | 4/2015 | Chen |
| 9,030,159 B2 | 5/2015 | Chen et al. |
| 9,031,665 B2 | 5/2015 | Aghassian |
| 9,031,666 B2 | 5/2015 | Fell |
| 9,101,768 B2 | 8/2015 | Khalil et al. |
| 9,101,774 B2 | 8/2015 | Mashiach et al. |
| 9,142,989 B2 | 9/2015 | Fell et al. |
| 9,155,900 B2 | 10/2015 | Meskens |
| 9,186,520 B2 | 11/2015 | Aghassian |
| 9,192,704 B2 | 11/2015 | Yomtov et al. |
| 9,209,634 B2 | 12/2015 | Cottrill et al. |
| 9,211,418 B2 | 12/2015 | Aghassian |
| 9,227,075 B2 | 1/2016 | Aghassian et al. |
| 9,259,584 B2 | 2/2016 | Bauhahn et al. |
| 9,314,642 B2 | 4/2016 | Ozawa et al. |
| 9,339,660 B2 | 5/2016 | Feldman et al. |
| 9,343,923 B2 | 5/2016 | Joshi |
| 9,354,620 B2 | 5/2016 | Ben-Shalom et al. |
| 9,356,473 B2 | 5/2016 | Ghovanloo |
| 9,427,509 B2 | 8/2016 | Vodermayer et al. |
| 9,435,830 B2 | 9/2016 | Joshi |
| 9,492,665 B2 | 11/2016 | Khalil et al. |
| 9,496,733 B2 | 11/2016 | Funderburk |
| 9,498,635 B2 | 11/2016 | Dellamano et al. |
| 9,555,257 B2 | 1/2017 | Mashiach et al. |
| 9,577,714 B2 | 2/2017 | Rehm |
| 9,673,393 B2 | 6/2017 | Pellizzer |
| 9,789,325 B2 | 10/2017 | Shelton et al. |
| 9,872,997 B2 | 1/2018 | Angara et al. |
| 9,878,170 B2 | 1/2018 | Angara et al. |
| 9,887,574 B2 | 2/2018 | Angara et al. |
| 10,363,426 B2 * | 7/2019 | Aghassian .......... H01F 27/2804 |
| 2002/0055763 A1 | 5/2002 | Zarinetchi et al. |
| 2003/0085684 A1 | 5/2003 | Tsukamoto et al. |
| 2003/0114899 A1 | 6/2003 | Woods et al. |
| 2004/0106963 A1 | 6/2004 | Tsukamoto et al. |
| 2004/0230247 A1 | 11/2004 | Stein et al. |
| 2005/0131486 A1 | 6/2005 | Boveja et al. |
| 2005/0187590 A1 | 8/2005 | Boveja et al. |
| 2005/0199716 A1 | 9/2005 | Shafer et al. |
| 2006/0122660 A1 | 6/2006 | Boveja et al. |
| 2006/0227989 A1 | 10/2006 | Polinske |
| 2006/0247737 A1 | 11/2006 | Olson et al. |
| 2007/0060980 A1 | 3/2007 | Strother et al. |
| 2007/0103617 A1 | 5/2007 | Kitajima et al. |
| 2007/0129767 A1 | 6/2007 | Wahlstrand |
| 2007/0185551 A1 | 8/2007 | Meadows et al. |
| 2008/0027293 A1 | 1/2008 | Vodermayer et al. |

(56) References Cited

U.S. PATENT DOCUMENTS

| | | |
|---|---|---|
| 2008/0027513 A1 | 1/2008 | Carbunaru |
| 2008/0046034 A1 | 2/2008 | Ibrahim |
| 2008/0172109 A1 | 7/2008 | Rahman et al. |
| 2008/0312530 A1 | 12/2008 | Malackowski et al. |
| 2009/0069869 A1 | 3/2009 | Stouffer et al. |
| 2009/0079270 A1 | 3/2009 | Jin |
| 2009/0082835 A1 | 3/2009 | Jaax et al. |
| 2009/0112291 A1 | 4/2009 | Wahlstrand et al. |
| 2009/0118796 A1 | 5/2009 | Chen et al. |
| 2009/0216068 A1 | 8/2009 | Thomas et al. |
| 2010/0305551 A1 | 12/2010 | Lobl et al. |
| 2010/0331917 A1 | 12/2010 | DiGiore et al. |
| 2010/0331918 A1 | 12/2010 | DiGiore et al. |
| 2010/0331919 A1 | 12/2010 | DiGiore et al. |
| 2011/0004278 A1 | 1/2011 | Aghassian et al. |
| 2011/0276111 A1 | 11/2011 | Carbunaru et al. |
| 2011/0301667 A1 | 12/2011 | Olson et al. |
| 2012/0012630 A1 | 1/2012 | Lui et al. |
| 2012/0063505 A1 | 3/2012 | Okamura et al. |
| 2012/0262108 A1 | 10/2012 | Olson et al. |
| 2012/0277831 A1 | 11/2012 | Joshi |
| 2013/0009665 A1 | 1/2013 | Clerc et al. |
| 2013/0023958 A1 | 1/2013 | Fell |
| 2013/0096651 A1 | 4/2013 | Ozawa et al. |
| 2013/0187598 A1 | 7/2013 | Park et al. |
| 2013/0197608 A1 | 8/2013 | Eiger |
| 2013/0214890 A1 | 8/2013 | Zabaco |
| 2014/0055088 A1 | 2/2014 | Joshi |
| 2014/0114373 A1 | 4/2014 | Aghassian |
| 2014/0203823 A1 | 7/2014 | Joshi |
| 2014/0266019 A1 | 9/2014 | Pigott |
| 2014/0324126 A1 | 10/2014 | Ozawa |
| 2014/0354211 A1 | 12/2014 | Zottola et al. |
| 2015/0028798 A1 | 1/2015 | Dearden et al. |
| 2015/0077050 A1 | 3/2015 | Funderburk |
| 2015/0236520 A1 | 5/2015 | Baarman |
| 2015/0231392 A1* | 8/2015 | Fell .................... A61N 1/08 607/61 |
| 2015/0360038 A1 | 12/2015 | Zottola et al. |
| 2016/0096028 A1 | 4/2016 | Aghassian |
| 2016/0126771 A1 | 5/2016 | Aghassian et al. |
| 2016/0263385 A1 | 9/2016 | Aghassian |
| 2016/0301239 A1 | 10/2016 | Funderburk |
| 2016/0367822 A1 | 12/2016 | Parramon |
| 2017/0151440 A1 | 6/2017 | Parramon et al. |
| 2017/0214268 A1 | 7/2017 | Howard |
| 2017/0214269 A1 | 7/2017 | Howard |
| 2017/0361113 A1 | 12/2017 | Aghassian et al. |
| 2017/0361115 A1 | 12/2017 | Aghassian et al. |

FOREIGN PATENT DOCUMENTS

| | | |
|---|---|---|
| EP | 0419729 | 4/1991 |
| EP | 2451526 | 6/2013 |
| WO | 2004/021876 | 3/2004 |
| WO | 2005/000391 | 1/2005 |
| WO | 2013/164831 | 11/2013 |

OTHER PUBLICATIONS

International Search Report and Written Opinion regarding corresponding PCT application No. PCT/US2017/036841, dated Aug. 17, 2017.

J. Miller et al., "Development of an Autotuned Transcutaneous Energy Transfer System," J. American Soc'y for Artificial Internal Organs (ASAIO), pp. M706-10 (1993).

Mitamura, Yoshinori, et al., "A Transcutaneous Optical Information Transmission System for Implantable Motor-Driven Artificial Hearts,"ASAIO Transactions, Bd. 36, Jul. 1, 1990, pp. 278-280.

Okamoto, Eiji, et al., "Development of a Bidirectional Transcutaneous Optical Data Transmission System for Artificial Hearts Allowing Long-Distance Data Communication with Low Electric Power Consumption," Journal of Artificial Organs—The Official Journal of the Japanese Society for Artificial Organs, Springer-Verlag, TO, Bd. 8, Nr. 3, Sep. 1, 2005, pp. 5 pages.

Zierhofer, C. M. et al., "Geometric Approach for Coupling Enhancement of Magnetically Coupled Coils," IEEE Transactions on Biomedical Engineering, vol. 43, No. 7, Jul. 1996, 7 pages.

* cited by examiner

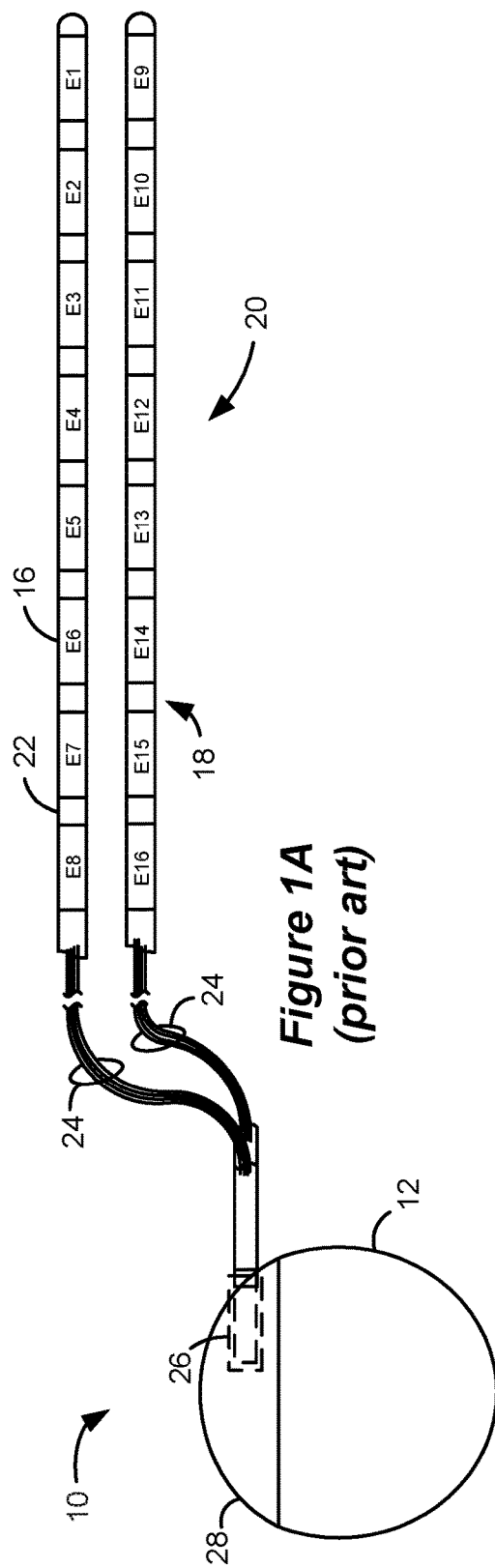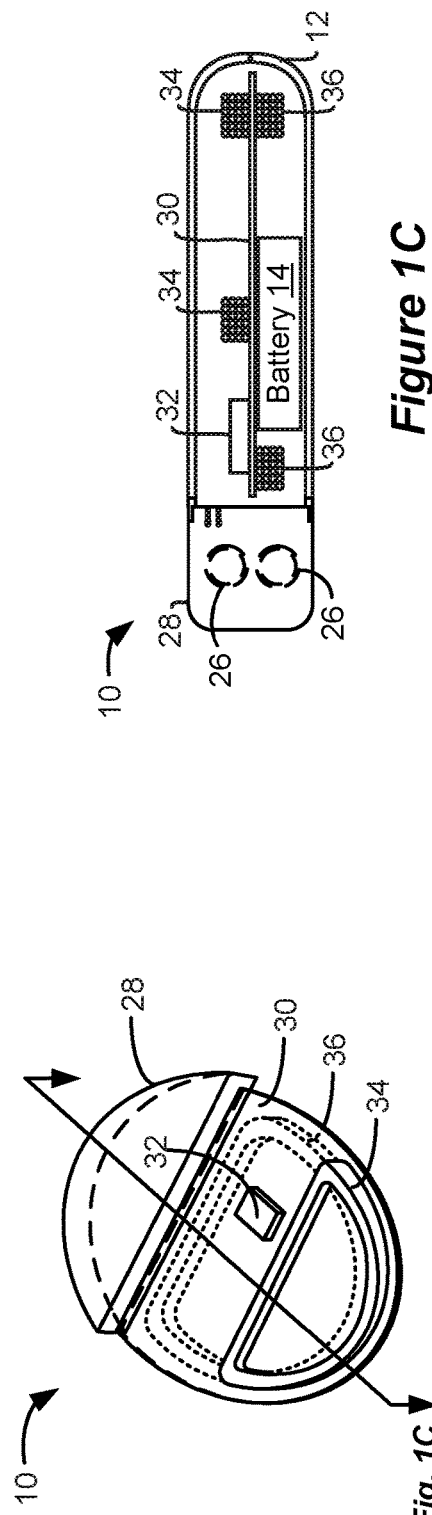
Figure 1A (prior art)
Figure 1B (prior art)
Figure 1C (prior art)

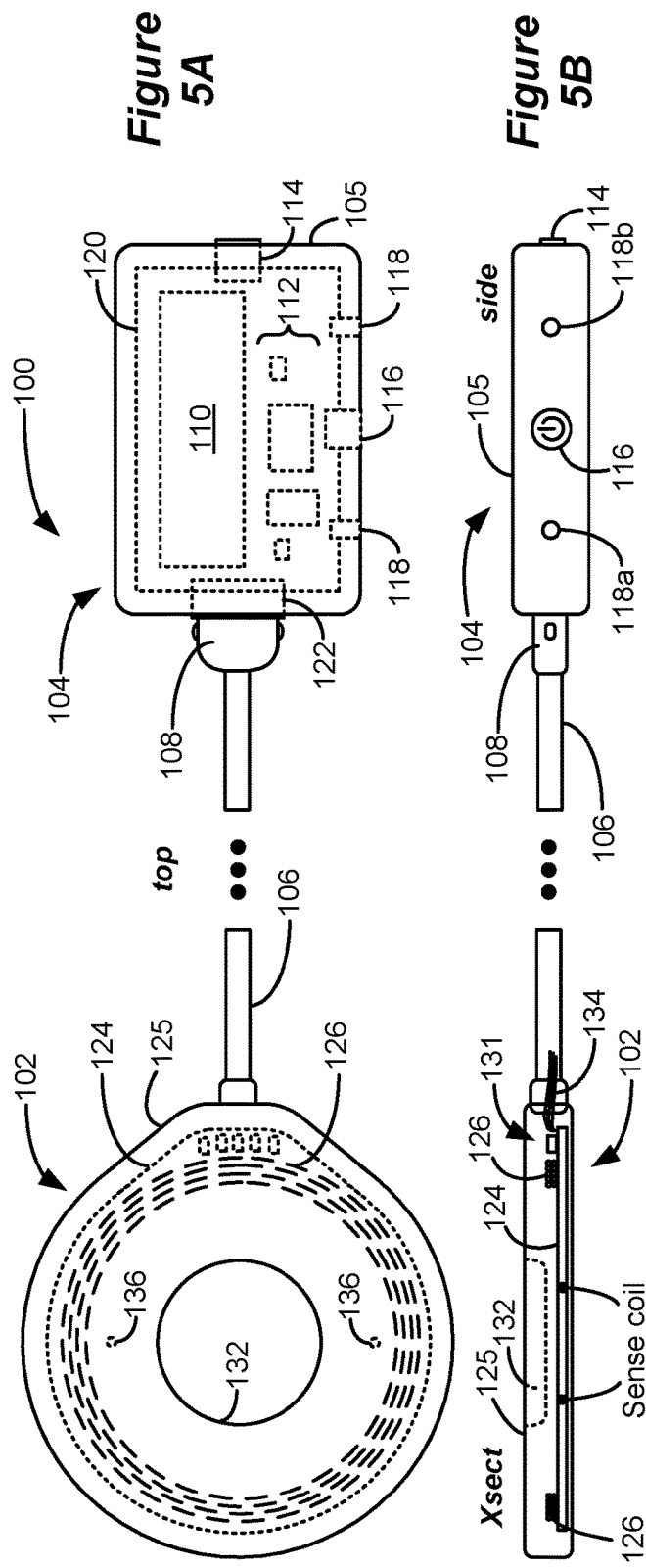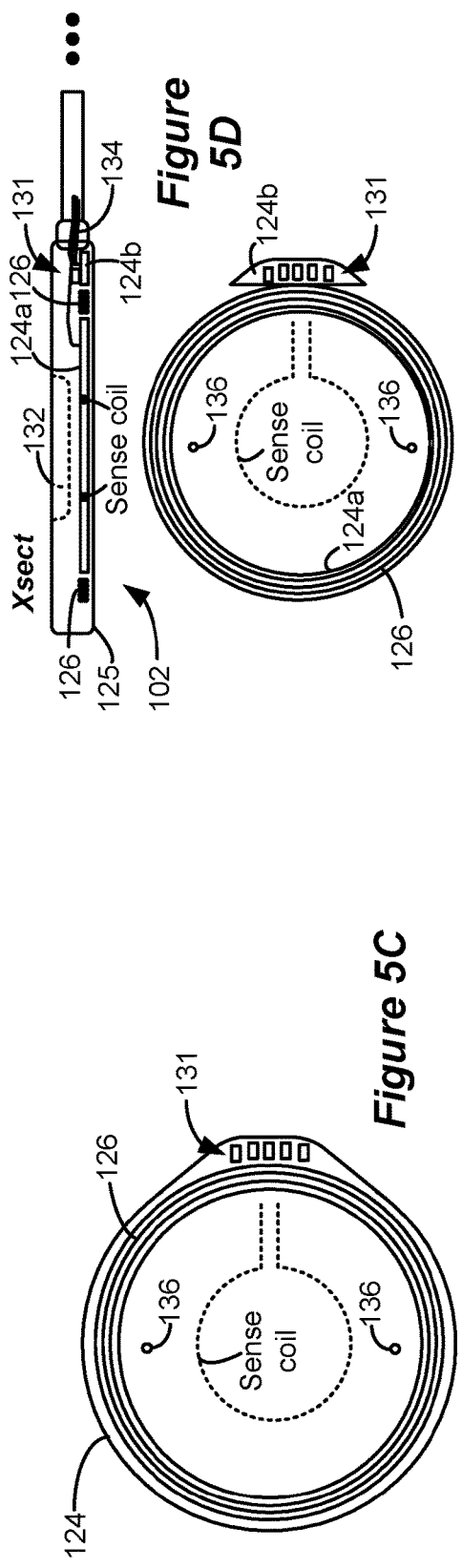

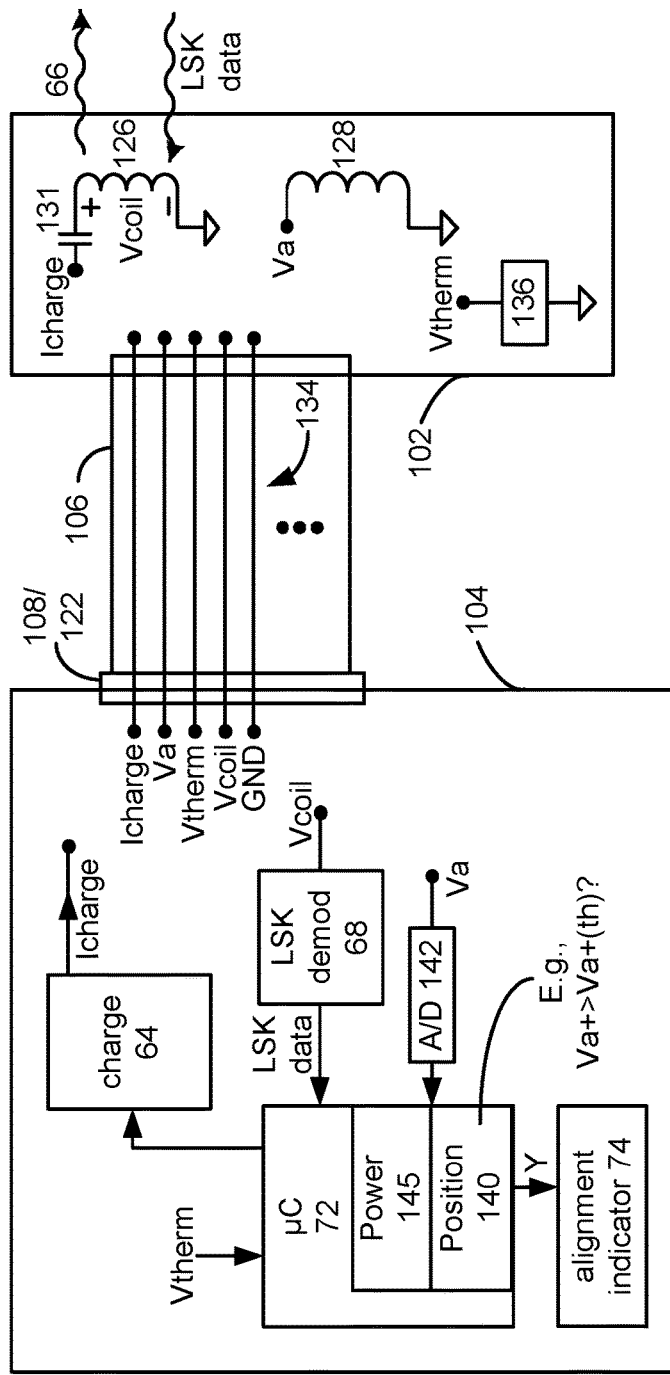
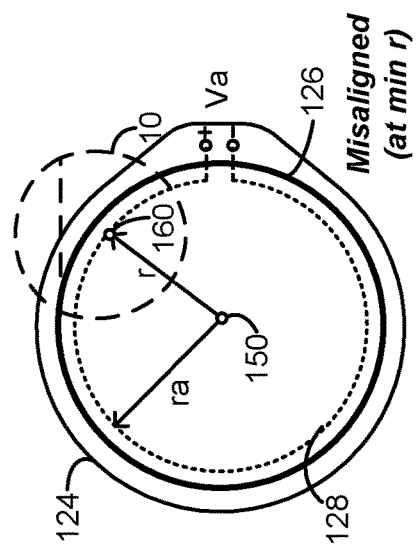
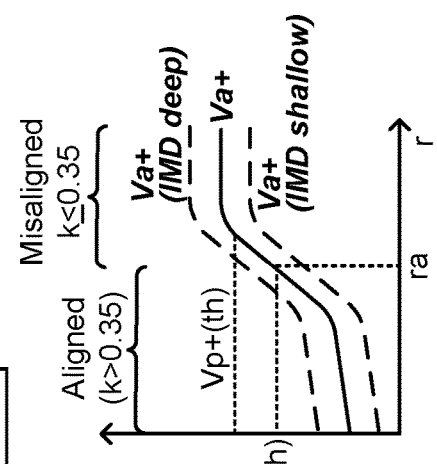
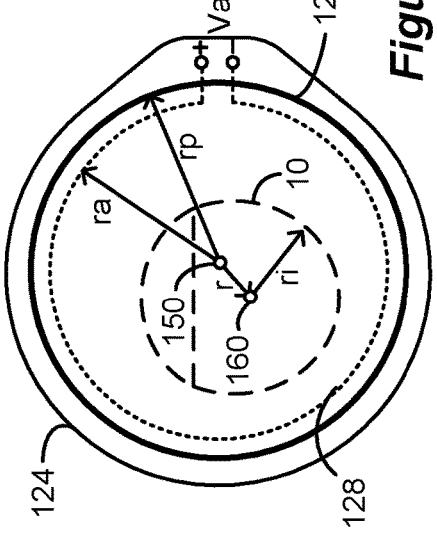
Figure 6A
Figure 6B
Figure 6C

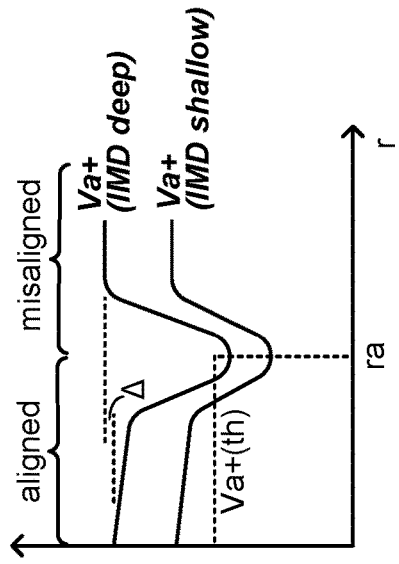
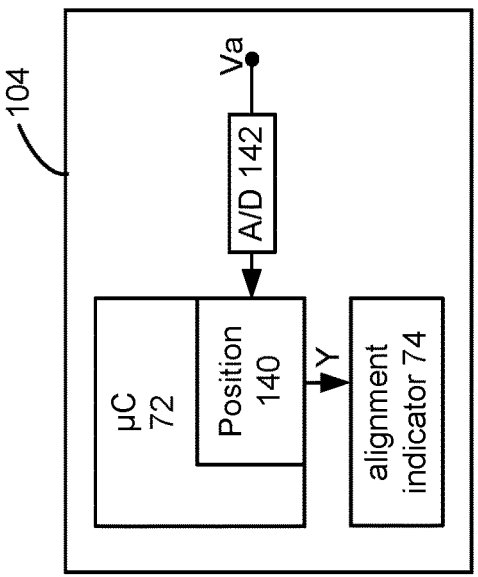
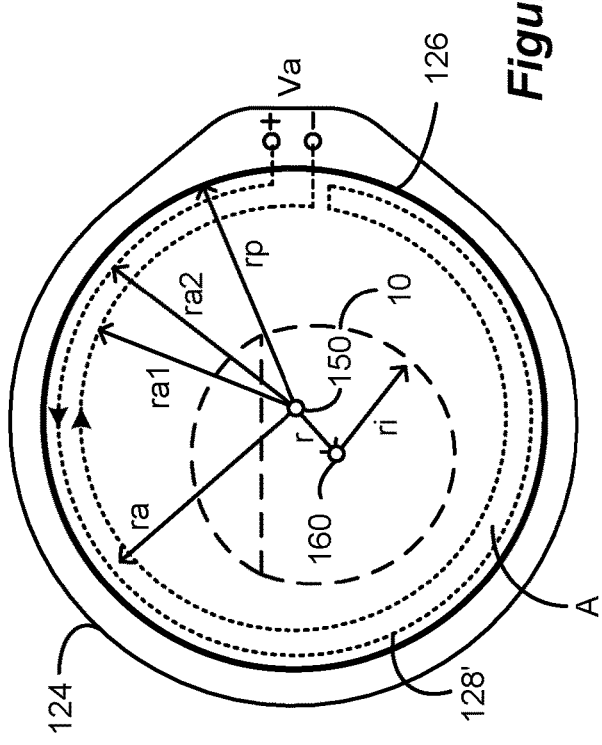
*Figure 7A*
*Figure 7C*
*Figure 7B*

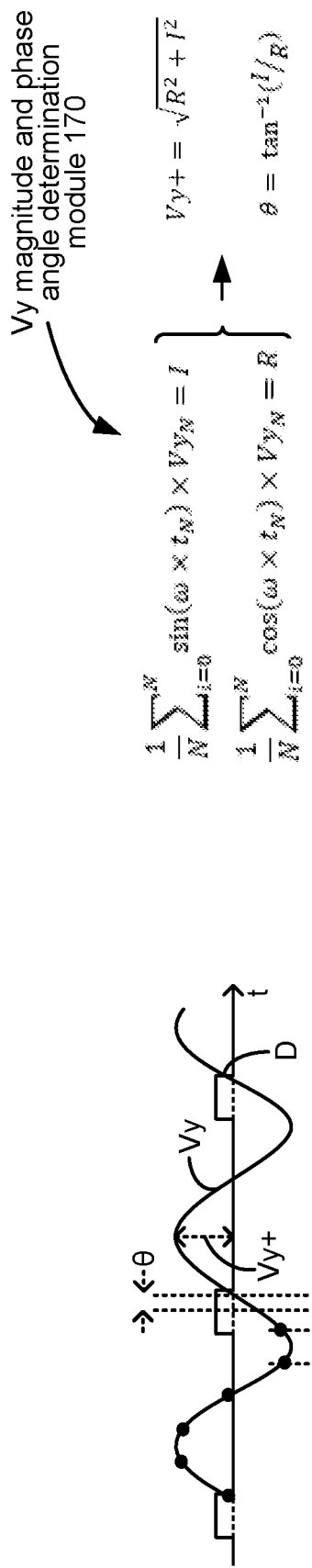
*Figure 13B*
*Figure 13C*
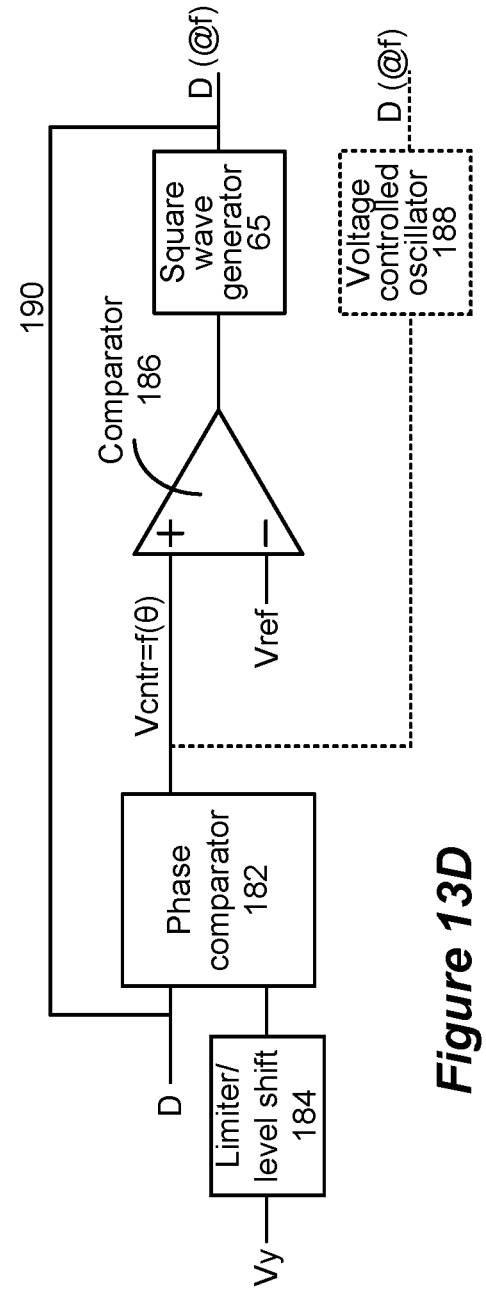
*Figure 13D*

EXTERNAL CHARGER FOR AN IMPLANTABLE MEDICAL DEVICE FOR DETERMINING POSITION USING PHASE ANGLE OR A PLURALITY OF PARAMETERS AS DETERMINED FROM AT LEAST ONE SENSE COIL

CROSS REFERENCE TO RELATED APPLICATIONS

This is a continuation application of U.S. patent application Ser. No. 15/616,543, filed Jun. 7, 2017 (allowed), which is a non-provisional of U.S. Provisional Patent Application Ser. No. 62/350,565, filed Jun. 15, 2016, which is hereby incorporated by reference in its entirety.

FIELD OF THE INVENTION

The present invention relates to wireless external chargers for use in implantable medical device systems.

BACKGROUND

Implantable stimulation devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability in any implantable medical device system, including a Deep Brain Stimulation (DBS) system.

As shown in FIGS. 1A-1C, a SCS system typically includes an Implantable Pulse Generator (IPG) 10 (Implantable Medical Device (IMD) 10 more generally), which includes a biocompatible device case 12 formed of a conductive material such as titanium for example. The case 12 typically holds the circuitry and battery 14 (FIG. 1C) necessary for the IMD 10 to function, although IMDs can also be powered via external RF energy and without a battery. The IMD 10 is coupled to electrodes 16 via one or more electrode leads 18, such that the electrodes 16 form an electrode array 20. The electrodes 16 are carried on a flexible body 22, which also houses the individual signal wires 24 coupled to each electrode. In the illustrated embodiment, there are eight electrodes (Ex) on each lead 18, although the number of leads and electrodes is application specific and therefore can vary. The leads 18 couple to the IMD 10 using lead connectors 26, which are fixed in a non-conductive header material 28, which can comprise an epoxy for example.

As shown in the cross-section of FIG. 1C, the IMD 10 typically includes a printed circuit board (PCB) 30, along with various electronic components 32 mounted to the PCB 30, some of which are discussed subsequently. Two coils (more generally, antennas) are show in the IMD 10: a telemetry coil 34 used to transmit/receive data to/from an external controller (not shown); and a charging coil 36 for charging or recharging the IMD's battery 14 using an external charger, which is discussed in detail later.

FIG. 2 shows the IMD 10 in communication with an external charger 50 used to wirelessly convey power to the IMD 10, which power can be used to recharge the IMD's battery 14. The transfer of power from the external charger 50 is enabled by a primary charging coil 52. The external charger 50, like the IMD 10, also contains a PCB 54 on which electronic components 56 are placed. Again, some of these electronic components 56 are discussed subsequently. A user interface 58, including touchable buttons and perhaps a display and a speaker, allows a patient or clinician to operate the external charger 50. A battery 60 provides power for the external charger 50, which battery 60 may itself be rechargeable. The external charger 50 can also receive AC power from a wall plug. A hand-holdable housing 62 sized to fit a user's hand contains all of the components.

Power transmission from the external charger 50 to the IMD 10 occurs wirelessly and transcutaneously through a patient's tissue 25, via inductive coupling. FIG. 3 shows details of the circuitry used to implement such functionality. Primary charging coil 52 in the external charger 50 is energized via charging circuit 64 with an AC current, Icharge, to create an AC magnetic charging field 66. This magnetic field 66 induces a current in the secondary charging coil 36 within the IMD 10, providing a voltage across coil 36 that is rectified (38) to DC levels and used to recharge the battery 14, perhaps via a battery charging and protection circuitry 40 as shown. The frequency of the magnetic field 66 can be perhaps 80 kHz or so. When charging the battery 14 in this manner, is it typical that the housing 62 of the external charger 50 touches the patient's tissue 25, perhaps with a charger holding device or the patient's clothing intervening, although this is not strictly necessary.

The IMD 10 can also communicate data back to the external charger 50 during charging using reflected impedance modulation, which is sometimes known in the art as Load Shift Keying (LSK). This involves modulating the impedance of the charging coil 36 with data bits ("LSK data") provided by the IMD 10's control circuitry 42 to be serially transmitted from the IMD 10 to the external charger 50. For example, and depending on the logic state of a bit to be transmitted, the ends of the coil 36 can be selectively shorted to ground via transistors 44, or a transistor 46 in series with the coil 36 can be selectively open circuited, to modulate the coil 36's impedance. At the external charger 50, an LSK demodulator 68 determines whether a logic '0' or '1' has been transmitted by assessing the magnitude of AC voltage Vcoil that develops across the external charger's coil 52 in response to the charging current Icharge and the transmitted data, which data is then reported to the external charger's control circuitry 72 for analysis. Such back telemetry from the IMD 10 can provide useful data concerning charging to the external charger 50, such as the capacity of the IMD's battery 14, or whether charging of the battery 14 is complete and operation of the external charger 50 and the production of magnetic field 66 can cease. LSK communications are described further for example in U.S. Patent Application Publication 2013/0096652.

External charger 50 can also include one or more thermistors 71, which can be used to report the temperature (expressed as voltage Vtherm) of external charger 50 to its control circuitry 72, which can in turn control production of the magnetic field 66 such that the temperature remains within safe limits. See, e.g., U.S. Pat. No. 8,321,029, describing temperature control in an external charging device.

Vcoil across the external charger's charging coil 52 can also be assessed by alignment circuitry 70 to determine how well the external charger 50 is aligned relative to the IMD 10. This is important, because if the external charger 50 is not well aligned to the IMD 10, the magnetic field 66 produced by the charging coil 52 will not efficiently be received by the charging coil 36 in the IMD 10. Efficiency in power transmission can be quantified as the "coupling" between the transmitting coil 52 and the receiving coil 36 (k, which ranges between 0 and 1), which generally speaking comprises the extent to which power expended at the transmitting coil 52 in the external charger 50 is received at the receiving coil 36 in the IMD 10. It is generally desired that the coupling between coils 52 and 36 be as high as possible: higher coupling results in faster charging of the IMD battery 14 with the least expenditure of power in the external charger 50. Poor coupling is disfavored, as this will require high power drain (e.g., a high Icharge) in the external charger 50 to adequately charge the IMD battery 14. The use of high power depletes the battery 60 in the external charger 50, and more importantly can cause the external charger 50 to heat up, and possibly burn or injure the patient.

Generally speaking, if the external charger 50 is well aligned with the IMD 10, then Vcoil will drop as the charging circuitry 64 provides the charging current Icharge to the charging coil 52. Accordingly, alignment circuitry 70 can compare Vcoil, preferably after it is rectified 76 to a DC voltage, to an alignment threshold, Vt. If Vcoil<Vt, then external charger 50 considers itself to be in good alignment with the underlying IMD 10. If Vcoil>Vt, then the external charger 50 will consider itself to be out of alignment, and can indicate that fact to the patient so that the patient can attempt to move the charger 50 into better alignment. For example, the user interface 58 of the charger 50 can include an alignment indicator 74. The alignment indicator 74 may comprise a speaker (not shown), which can "beep" at the patient when misalignment is detected. Alignment indicator 74 can also or alternatively include one or more Light Emitting Diodes (LED(s); not shown), which may similarly indicate misalignment.

Charger-to-IMD coupling depends on many variables, such as the permeability of the materials used in the external charger 50 and the IMD 10, as well materials inherent in the environment. Coupling is also affected by the relative positions of the external charger 50 and IMD 10, as shown in FIGS. 4A-4C. For best coupling (higher values of k), it is preferred that axes around which coils 52 and 36 are wound (52' and 36') are parallel and collinear, with the coils 52 and 36 as close as possible (d1) to each other, as shown in FIG. 4A. Distance d1 indicates the depth between the external charger 50 and the IMD 10, and is generally constant given that the external charger is generally placed on the patient's tissue 25, and that the IMD 10 has been implanted at a particular depth. Deviations from these ideal conditions will generally reduce coupling, as shown in FIGS. 4B-4C. In FIG. 4B for instance, the coil axes 52' and 36' are not collinear, but instead are laterally offset (x). In FIG. 4C, the coil axes 52' and 36' are parallel and collinear, but the IMD 10 is relatively deep (d2). In any of these non-ideal cases, coupling will be reduced, meaning that the IMD's battery 14 will not charge as quickly, or that the external charger 50 must output more power (e.g., Icharge must be higher) to affect the same charging rate of the IPG's battery 14.

It should be noted with reference to FIG. 4C that the depth d2 of the IMD 10 cannot generally be changed, as this parameter results from how the IMD 10 was implanted in the patient. As a result, the external charger 50 may be in alignment with the IMD 10, even if the coupling between the external charger 50 and the IMD 10 is relatively poor (and thus Vcoil is relatively high). It can be useful to adjust the alignment threshold Vt (i.e., upwards) used by the alignment circuitry 70 in such cases so that the external charger 50 will not unreasonably indicate misalignment to the patient when there is nothing the patient can do to improve alignment. U.S. Pat. No. 9,227,075 describes one technique for adjusting Vt to address alignment as a function of implant depth, although this technique is not described here.

BRIEF DESCRIPTION OF THE DRAWINGS

FIGS. 1A-1C show different views of an implantable pulse generator, a type of implantable medical device (IMD), in accordance with the prior art.

FIG. 2 shows an external charger being used to charge a battery in an IMD, while

FIGS. 5A-5E show an improved charging system having a charging coil assembly and an electronics module, with FIGS. 5B-5E showing use of one or more sense coils with a charging coil in the charging coil assembly, in accordance with examples of the invention.

FIGS. 6A-6C show use of a first alignment sense coil of a constant radius in the charging coil assembly, as well as circuitry for detecting and indicating misalignment between the charging coil and the IMD, in accordance with an example of the invention.

FIGS. 7A-7C show use of a second alignment sense coil having edge detection capability in the charging coil assembly, as well as circuitry for detecting and indicating misalignment between the charging coil and the IMD, in accordance with an example of the invention.

FIG. 12A shows an algorithm operable in the charging system for determining alignment and centering, and for controlling the magnetic field produced by the charging coil, while

FIG. 13A shows modified position circuitry for the charger system able to determine IMD-to-charger positioning using one of more of the sense coil parameters of magnitude, phase angle, and resonant frequency, while FIGS. 13B-13D show circuitry and manners in which these parameters can be determined or measured, in accordance with an example of the invention.

Figure 13A:
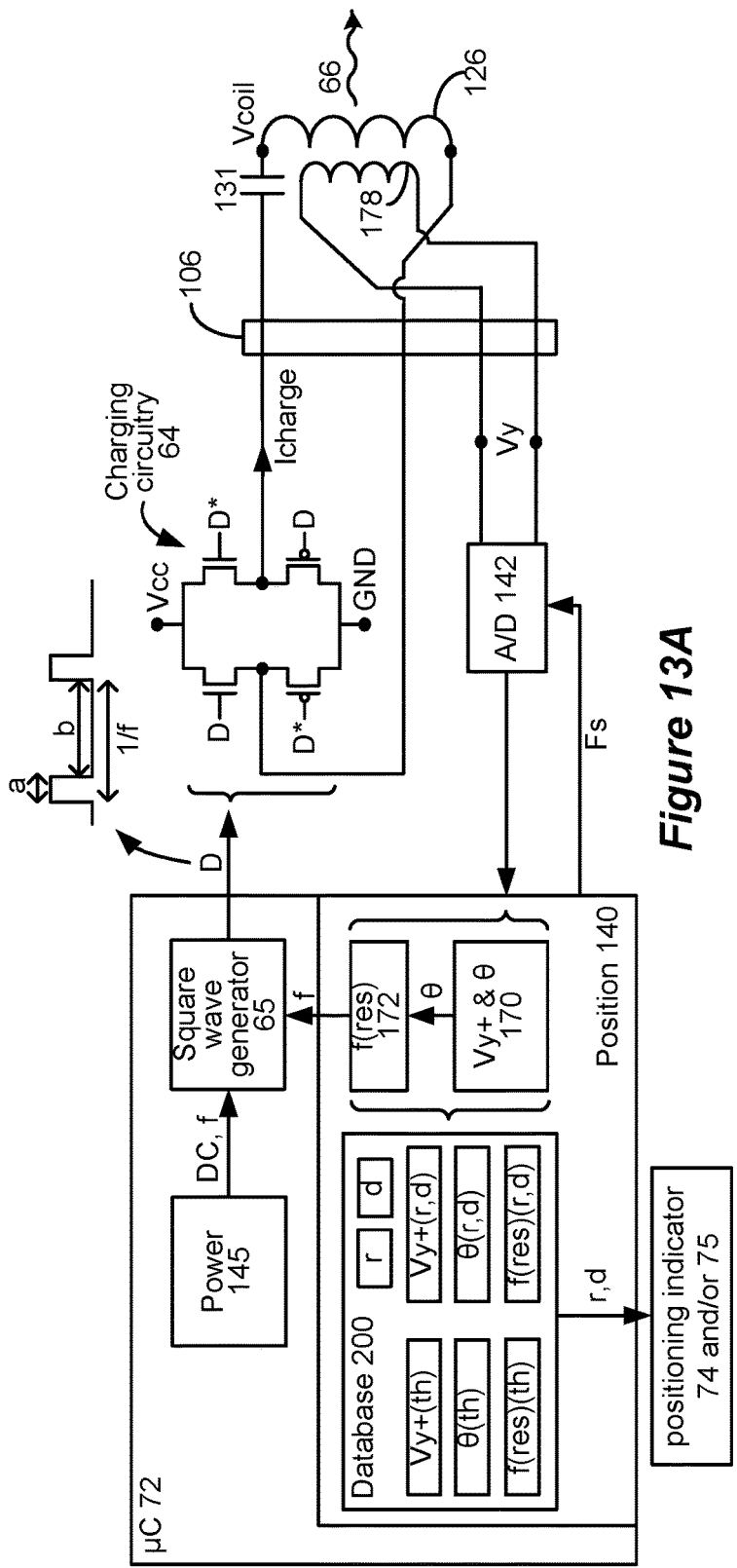
Figure 14A:
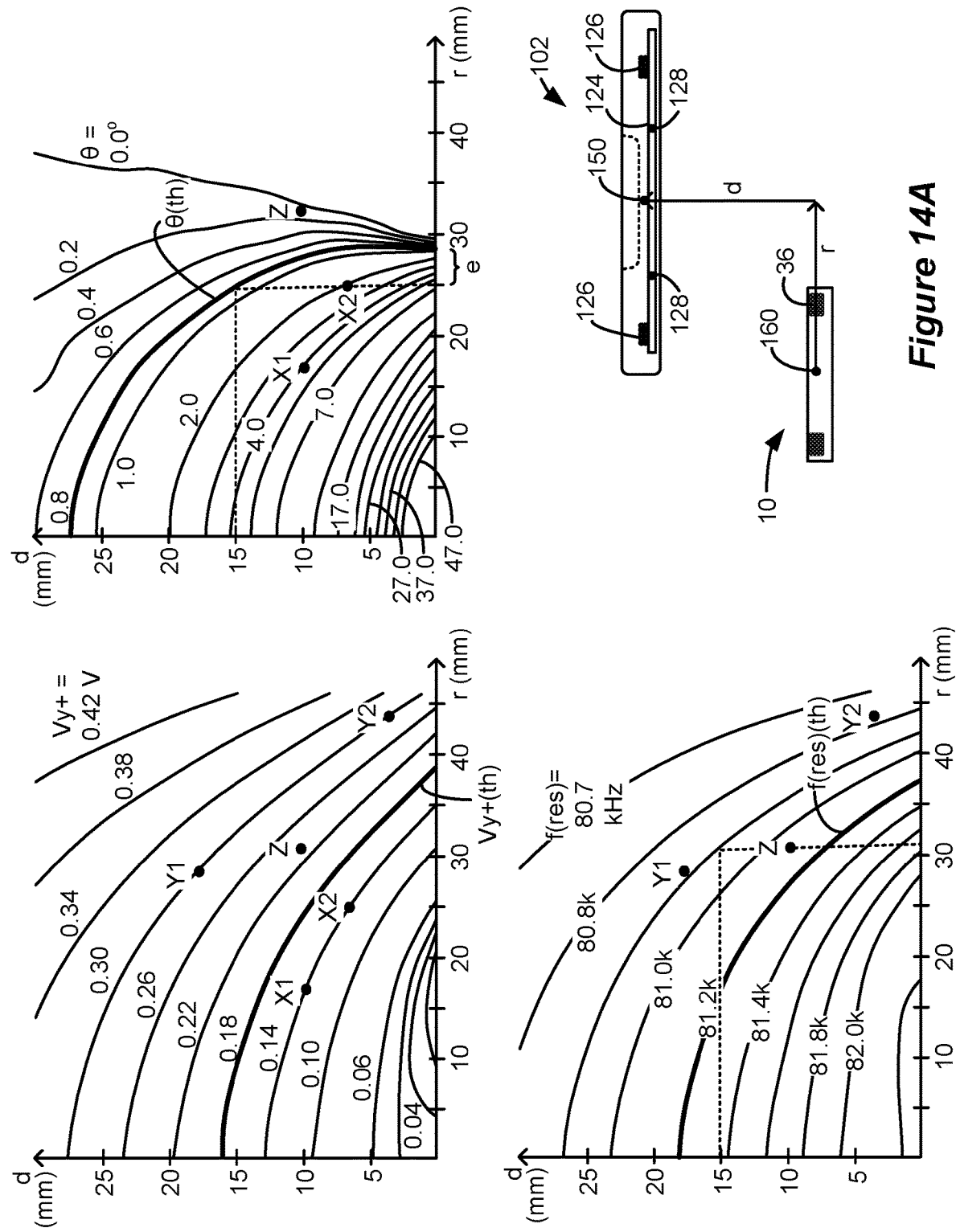
Figure 14B:
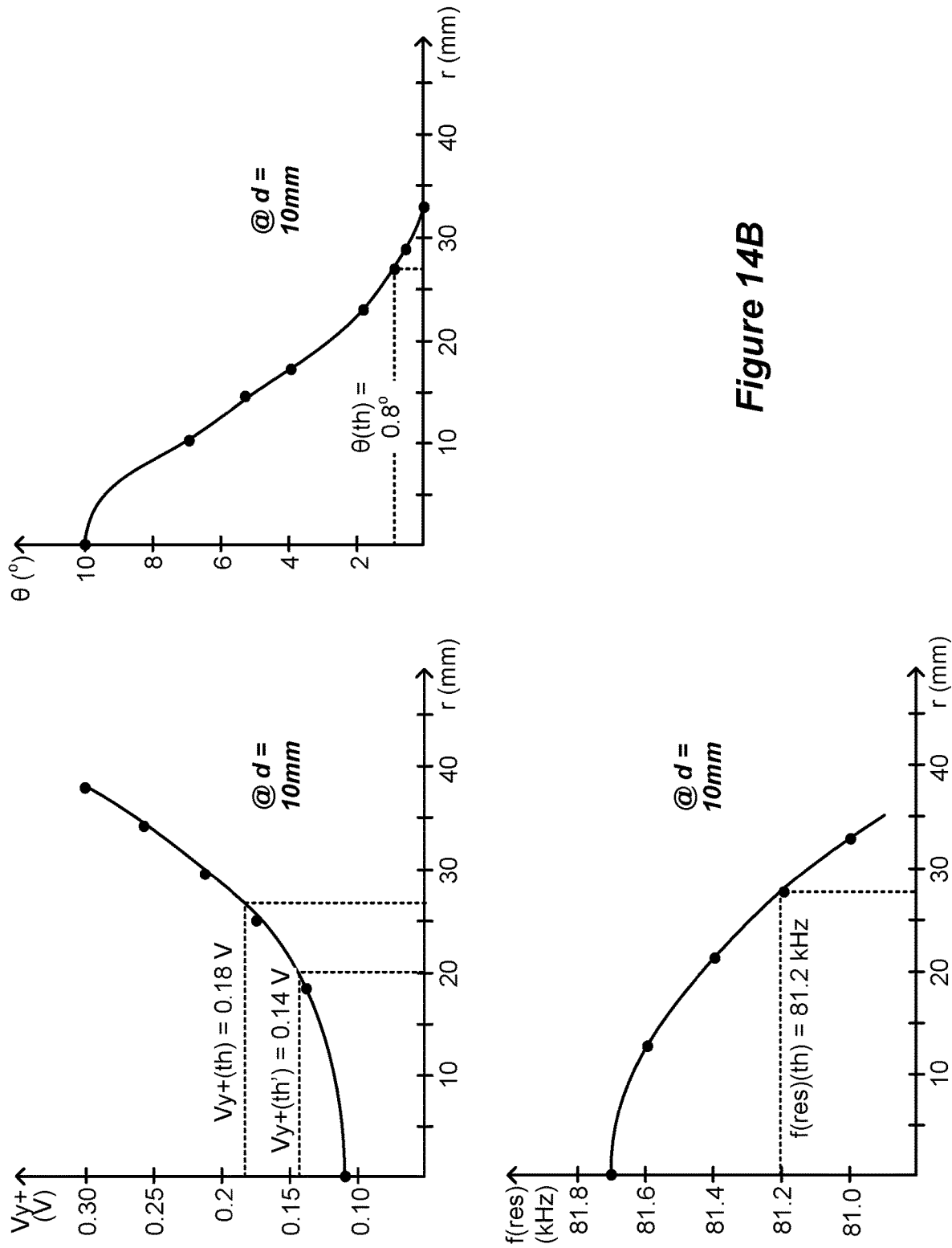

FIGS. 14A and 14B show contours of experimentally-determined data relating the sense coil parameters of magnitude, phase angle, and resonant frequency to charger-to-IMD radius and depth, as useful in the modified position circuitry of FIG. 13A, in accordance with an example of the invention.

Figure 15A:
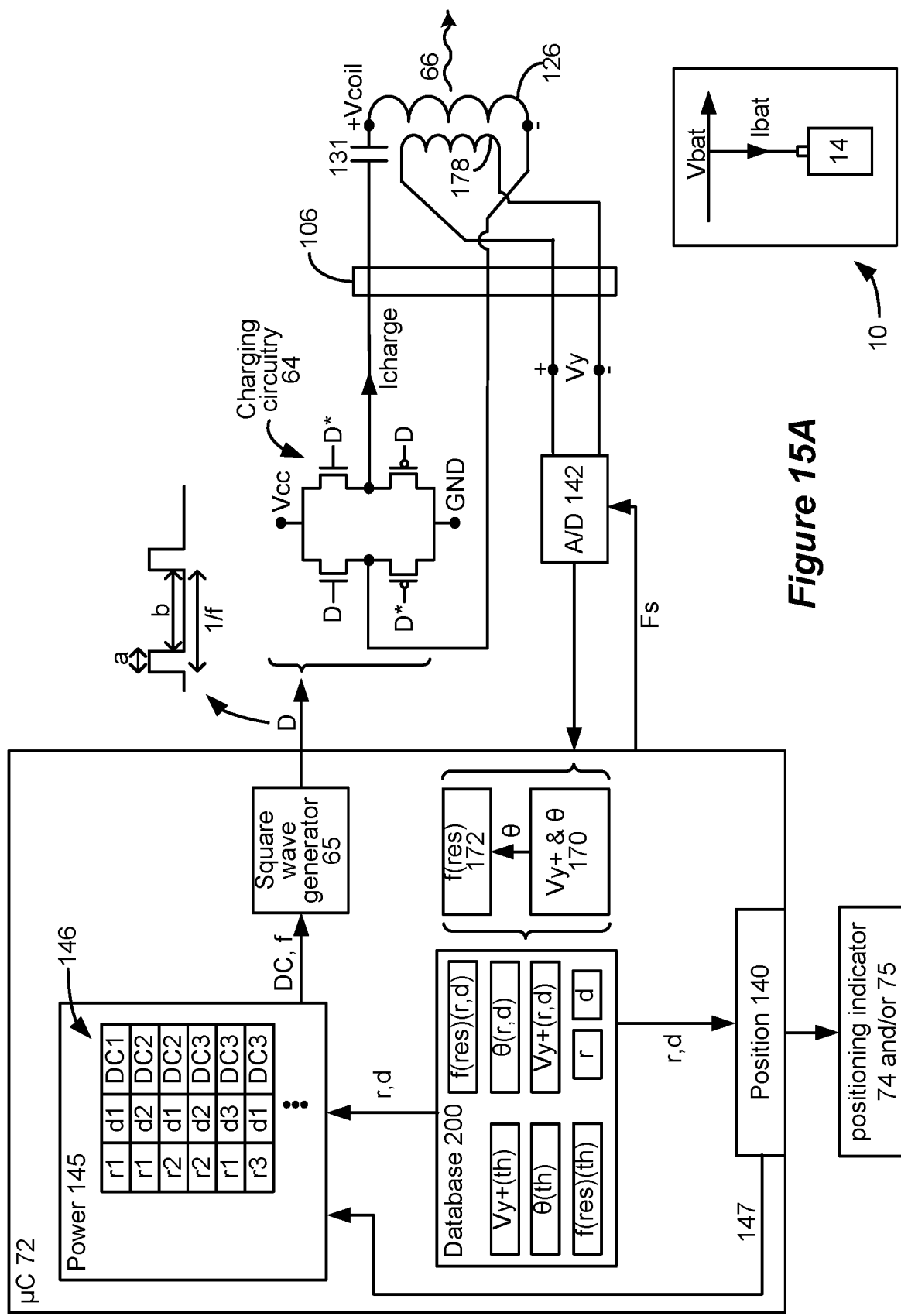
Figure 15B:
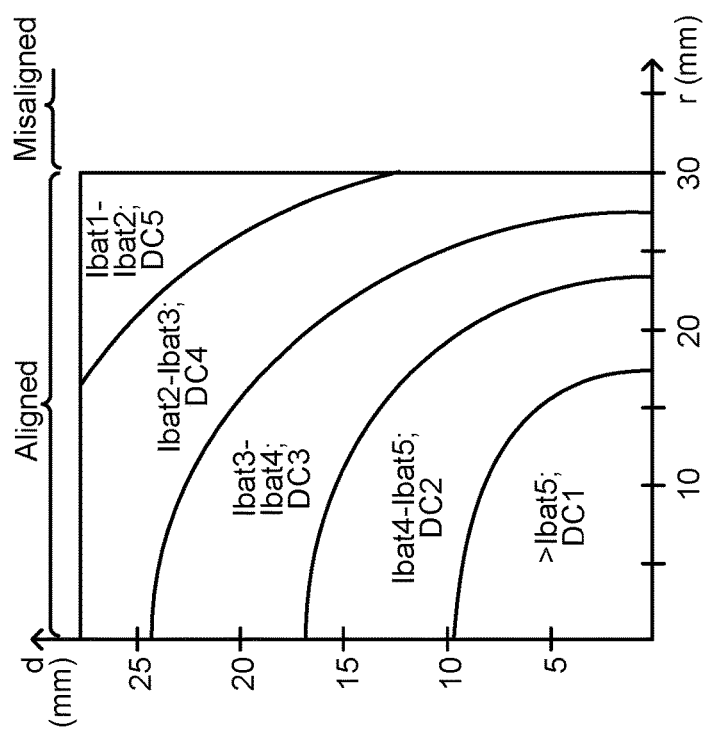

FIG. 15A shows power circuitry for the charger system able to adjust magnetic field power using one of more of the sense coil parameters of magnitude, phase angle, and resonant frequency, while FIG. 15B shows experimentally how charger-to-IMD position affects power received at the IMD, in accordance with an example of the invention.

Figure 16:
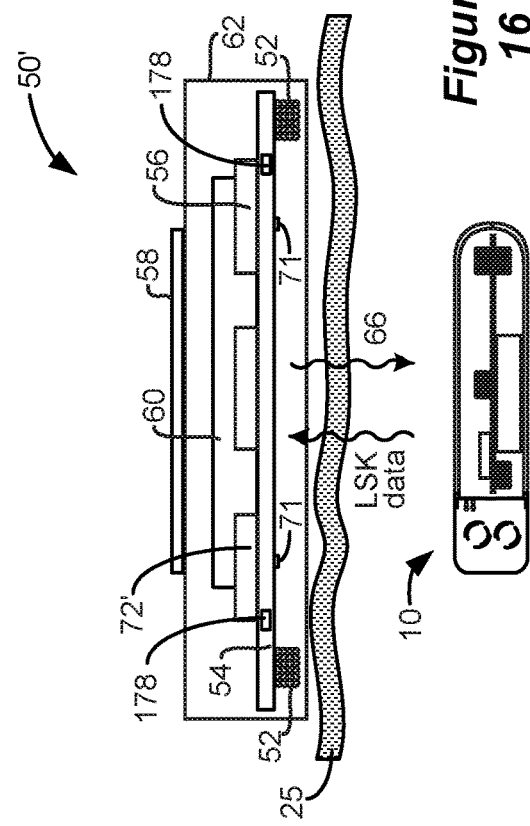

FIG. 16 shows an integrated external charger in which the electronics, charging coil, and sense coil(s) are housed in a single housing, in accordance with an example of the invention.

FIGS. 17A-17E show the use of additional sense coils arranged in manners to provide information regarding one or more direction by which the charging coil 126 is misaligned or non-centered with respect to an IMD, in accordance with examples of the invention.

Figure 18:
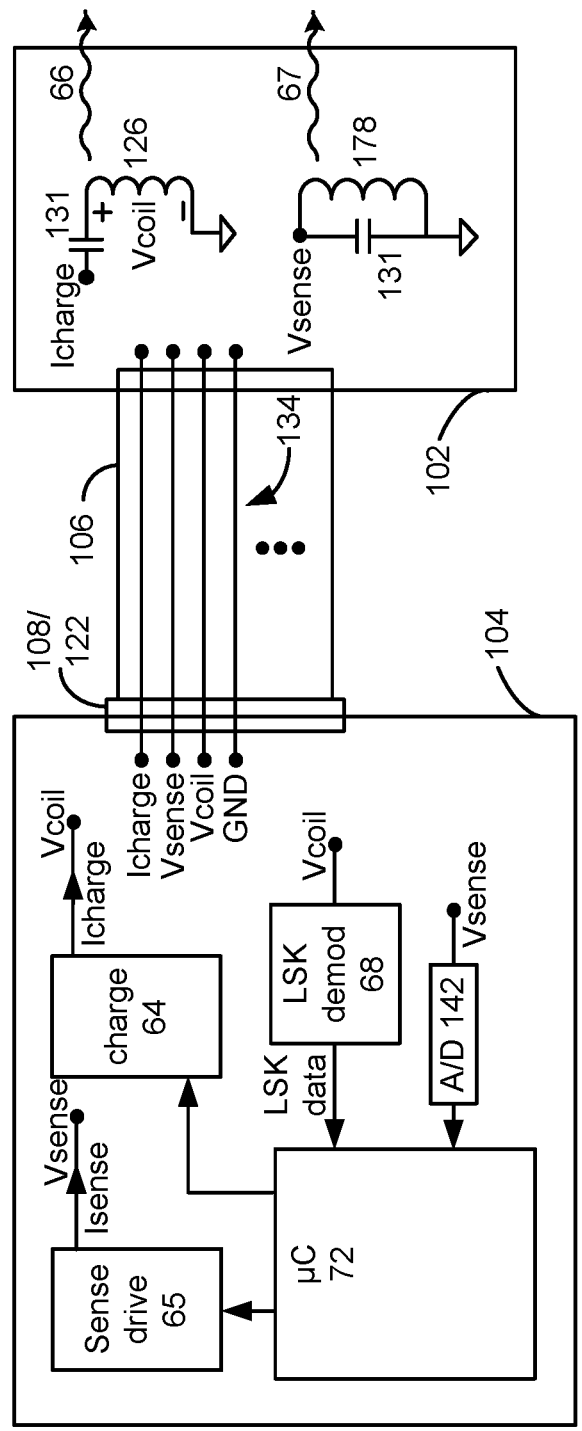

FIG. 18 shows how one or more sense coils in the charging system can be actively driven to determine charger-to-IMD positioning and/or how magnetic field power can be adjusted, in accordance with an example of the invention.

Figure 19:
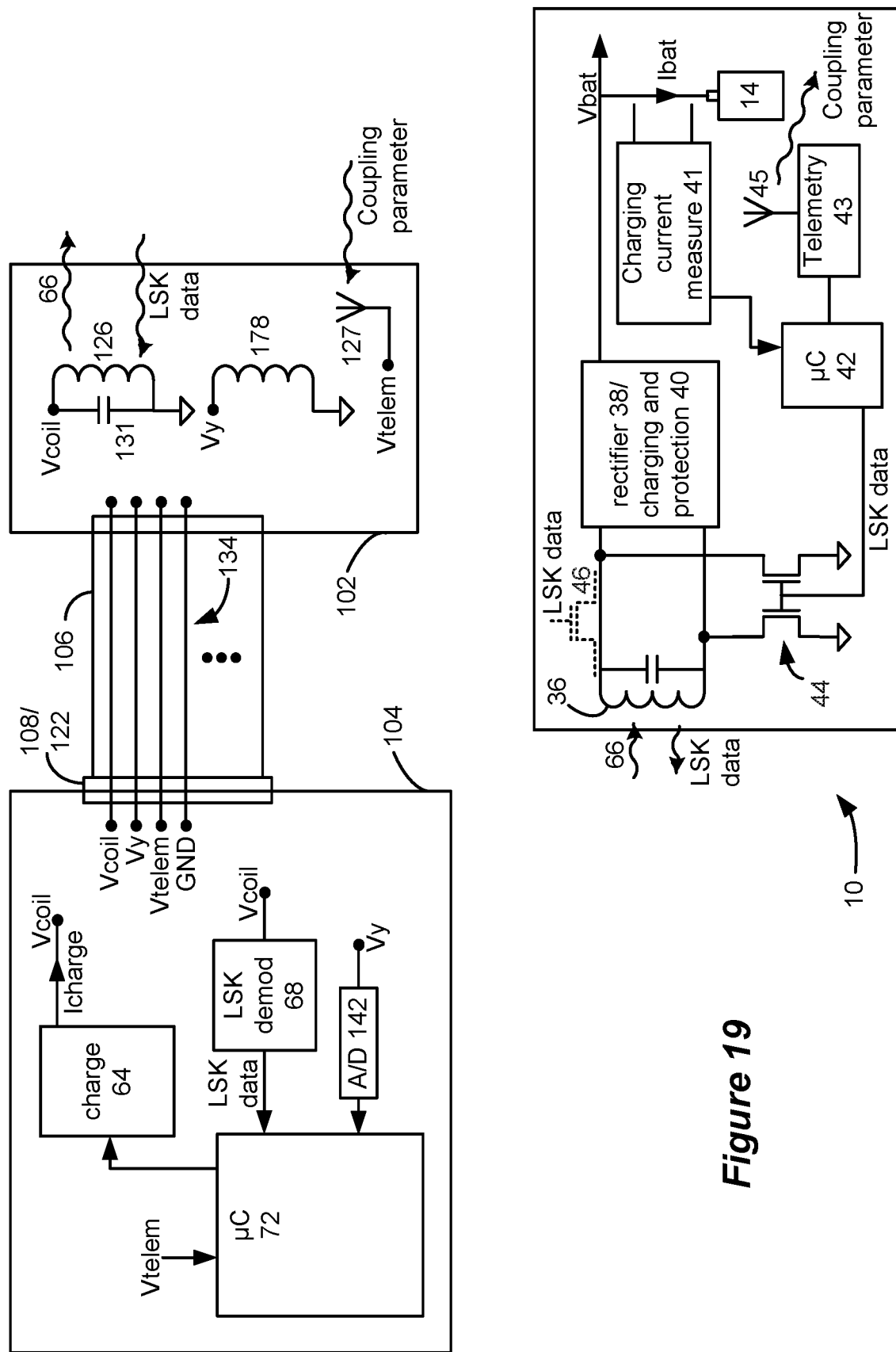

FIG. 19 shows how charger-to-IMD positioning and/or magnetic field power adjustment can be assisted by the provision of hardware enabling the IMD to telemeter a coupling parameter to the charging system, in accordance with an example of the invention.

DETAILED DESCRIPTION

An improved charging system 100 for an IMD 10 is shown in FIG. 5A. Charging system 100 includes two main parts: an electronics module 104 and a charging coil assembly 102 which includes a charging coil 126. The electronics module 104 and the charging coil assembly 102 are connected by a cable 106. The cable 106 may be separable from both the electronics module 104 and the charging coil assembly 102 via a port/connector arrangement, but as illustrated cable 106 is permanently affixed to the charging coil assembly 102. The other end of the cable 106 includes a connector 108 that can attach to and detach from a port 122 of the electronics module 104.

Electronics module 104 preferably includes within its housing 105 a battery 110 and active circuitry 112 needed for charging system operation, some of which are described subsequently. Electronics module 104 may further include a port 114 (e.g., a USB port) to allow its battery 110 to be recharged in conventional fashion, and/or to allow data to be read from or programmed into the electronics module, such as new operating software. Housing 105 may also carry a user interface, which as shown in the side view of FIG. 5B can include an on/off switch to begin/terminate generation of the magnetic field 66, and one or more LEDs 118a and 118b. In one example, LED 118a is used to indicate the power status of the electronics module 104. For example, LED 118a may be lit when its battery 110 is charged, and may blink to indicate that the battery 110 needs charging. LED 118b may operate as explained further below. More complicated user interfaces, such as those incorporating a speaker and a display, could also be used. User interface elements can be included on other faces of the electronic module's housing 105, and may be placed such that they are easily viewed for the therapeutic application at hand (e.g., SCS, DBS). Electronics are integrated within the housing 105 of the electronics module 104 by a circuit board 120.

Charging coil assembly 102 preferably contains only passive electronic components that are stimulated or read by active circuitry 112 within the electronics module 104. Such components include the primary charging coil 126 already mentioned, which as illustrated comprises a winding of copper wire and is energized by charging circuitry 64 (FIG. 6A) in the electronics module 104 to create the magnetic charging field 66 that provides power to the IMD 10, such as may be used to recharge the IMD 10's battery 14. Further included within the charging coil assembly 102 are one or more sense coils. As explained in detail later, the one or more sense coils are measured in various ways to perform different functions in the charging system 100. For example, sense coil measurements can be used to determine the position of the charging coil 126 (charging coil assembly 102) with respect to the IMD 10 being charged, and more specifically whether the charging coil 126 is aligned and/or centered with respect to an IMD 10 being charged. Sense coil measurements can also be used to adjust the power of the magnetic field 66 provided by the charging coil 126.

As shown in the cross section of FIG. 5B, the one or more sense coils are preferably formed using one or more traces in a circuit board 124, which circuit board 124 is also used to integrate the electronic components within the charging coil assembly 102. Circuit board 124 is shown in isolation in FIG. 5C. While it is preferred that charging coil 126 comprise a wire winding, and that the one or more sense coils comprise traces within the circuit board 124, this is not strictly necessary: the charging coil 126 can also be formed from traces in circuit board 124, and the one or more sense coils can comprise wire windings. Note that the charging coil 126 and the one or more sense coils, as well as being concentric, are also formed in planes that are parallel, and can also be formed in the same plane as discussed further below with respect to FIG. 5D.

Further passive components preferably included within the charging coil assembly 102 include one or more tuning capacitors 131. As shown in later circuit diagrams (e.g., FIG. 6A), a capacitor 131 is coupled to the charging coil 126 to tune the resonant frequency of this L-C circuit (e.g., to 80 kHz). One skilled in the art will understand that the value of the capacitor 131 (C) connected to the charging coil 126 will be chosen depending on the inductance (L) of that coil, in accordance with the equation $f(res)=1/sqrt(2\pi LC)$. Each of the one or more sense coils may also be coupled to a tuning capacitor 131, although this is not necessary and is not shown in further circuit diagrams. A tuning capacitor 131 can be placed in series or in parallel with its associated coil, although a series configuration is shown in subsequent figures.

The charging coil assembly 102 can further include one or more temperature sensors, such as thermistors 136, which can be used to report the temperature of the charging coil assembly 102 to the electronics module 104 (FIG. 6A, Vtherm). Such temperature data can in turn control production of the magnetic field 66 such that the temperature remains within safe limits. See, e.g., U.S. Pat. No. 8,321,029, describing temperature control in an external charging device.

Electronic components within the charging coil assembly 102 can be integrated differently. In FIGS. 5B and 5C, a single circuit board 124 is used, with the charging coil 126 mounted to the patient-facing side of the circuit board 124, and with wires 134 in the cable 106 preferably coupled to the circuit board 124. In FIG. 5D however, two circuit boards 124a and 124b are used. Circuit board 124b is outside of the area of the charging coil 126, and includes capacitors 131. Circuit board 124a is within the area of the charging coil 126, and includes the one or more sense coils and the thermistors 136. In the two-circuit-board 124a and 124b arrangement of FIG. 5D, notice in the cross section that the charging coil 126 and circuit boards 124a and 124b can be generally located in the same plane, which allows for a thinner construction of the charging coil assembly 102. In FIG. 5D, the wires 134 within the cable 106 can connect to both circuit boards 124a and 124b to allow communication between the components and the electronics module 104. The two circuit boards 124a and 124b can also have connections between them (not shown).

Components in the charging coil assembly 102 are integrated within a housing 125, which may be formed in different ways. In one example, the housing 125 may include top and bottom portions formed of hard plastic that can be screwed, snap fit, ultrasonic welded, or solvent bonded together. Alternatively, housing 125 may include one or more plastic materials that are molded over the electronics components. One side of the housing 125 may include an indentation 132 to accommodate the thickness of a material (not shown) that can be useful to affixing the charging coil assembly 102 to the patient, to the patient's clothes, or within a holding device such as a charging belt or harness. See, e.g., U.S. Patent Application Publication 2016/0301239, disclosing a belt for holding a charging coil assembly and control module that can be used with charging system 100. Such material may include Velcro or double-sided tape for example.

Figure 5E:
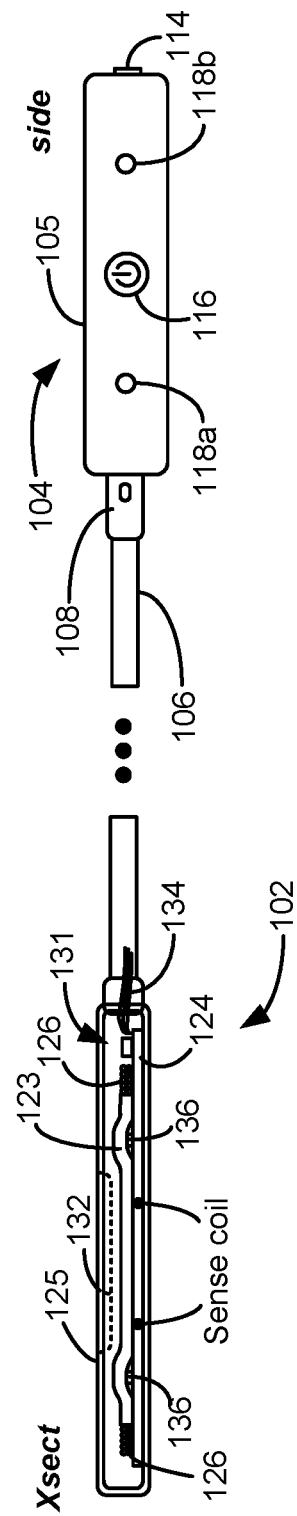

FIG. 5E shows another example of charging coil assembly 102. This example shows the one or more thermistors 136 on the top of the PCB 124 along with the charging coil 126 and other components, such as the one or more tuning capacitors 131. To assist with temperature detection, a thermal diffuser 123 is included, as disclosed in U.S. Provisional Patent Application Ser. No. 62/514,304, filed Jun. 2, 2017. The thermal diffuser 123 is shown within and in contact with the charging coil 126, but could cover the charging coil 126 or appear outside of the charging coil 126 as well. As its name implies, thermal diffuser 123 helps to conduct heat generated by excitation of the charging coil 126 and generation of the magnetic charging field 66, and thus provides a more-uniform temperature to each of the thermistor(s) 136. In one example, the thermal diffuser 123 comprises a deformable layer with a sticky side that can be pressed onto to the PCB 124 and over the thermistor(s) 136, such as Thermally Conductive Acrylic Interface Pad Part No. 5590H, manufactured by 3M Company. In a preferred example, there are four thermistors 136, each equally placed on the PCB 124 at 90-degrees inside the charging coil 126. In the example of FIG. 5E, the underside of the PCB 124 is generally flat, and has no components or other structures applied to it. As a result, this underside may directly contact the inner surface of bottom portion of housing 125. Note that the relative lack of components in charging coil assembly 102 means that either the top or bottom of the charging coil assembly 102 may face the patient during charging of his IMD 10.

Figure 3:
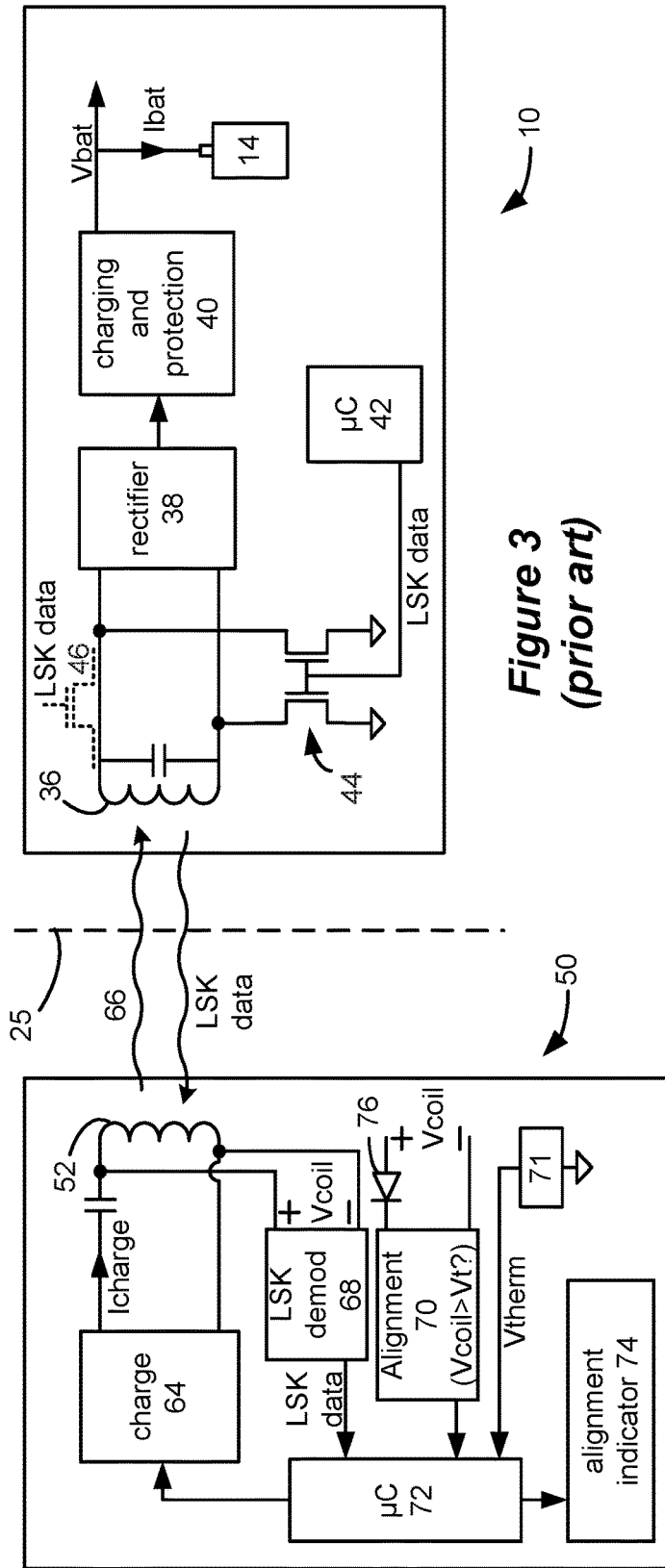
FIG. 3 shows circuitry in both, in accordance with the prior art.

Before discussing operation of the one or more sense coils, other aspects of charging system 100 shown in FIG. 6A can be appreciated. Like the external charger 50 described earlier (FIG. 3), the electronics module 104 may include (as part of circuitry 112; FIG. 5A) control circuitry 72 that controls charging circuitry 64 to generate a charging current, Icharge. This current is passed via connector/port 108/122 through a wire 134 in cable 106 to energize the charging coil 126 to produce the magnetic field 66. The resulting voltage across the charging coil 126, Vcoil, perhaps as dropped in voltage using a voltage divider, can be monitored for LSK communication from the IMD 10 with the assistance of LSK demodulator 68. And again, one or more indications of temperature (Vtherm) can be reported from the one or more thermistors 136 in the charging coil assembly 102 to allow the control circuitry 72 to control production of the magnetic field 66 as mentioned previously. Such conventional aspects can be used in all examples of the charging system 100, and are not discussed or illustrated in subsequent examples.

While it is preferable to place control circuitry 72 and other circuitry 112 aspects in the electronics module 104, this is not strictly necessary, and instead such components can reside in the charging coil assembly 102, for example, on its circuit board 124. Thus, electronics module 104 may retain only battery 110 and user interface aspects. Control circuitry 72 can comprise a microcontroller programmed with firmware, such as any of the STM32F4 ARM series of microcontrollers provided by STMicroeletronics, Inc., as described at http://www.st.com/content/st_com/en/products/microcontrollers/stm32-32-bit-arm-cortex-mcus/stm32f4-series.html?querycriteria=productId=SS1577. Control circuitry 72 may also comprise an FPGA, DSP, or other similar digital logic devices, or can comprise analog circuitry at least in part as explained further below. Control circuitry 72 can further comprise a memory programmed with firmware and accessible to a microcontroller or other digital logic device should that logic device not contain suitable on-chip memory.

In a first example shown in FIGS. 6A-6C, the charging system 100 includes circuitry 140 to determine a position of the charging coil 126 in the charging coil assembly 102 with respect to an underlying IMD 10 that is being charged. Position circuitry 140 in this example comprises part of control circuitry 72, and thus may operate digitally as programmed firmware, although position circuitry 140 can also comprise analog components as explained further below.

Charger-to-IMD positioning, as explained further below, can determine for example whether the charging coil 126 and the IMD 10 are "aligned" or "centered." The border between alignment and misalignment refers to whether or not the positioning between the charging coil 126 (the charging coil assembly 102 more generally) and the IMD 10, and hence their coupling, is significantly poor such that the charging coil 126 will no longer adequately charge the IMD's battery 14. For example, the charging coil 126 can be said to be aligned with the IMD 10 if the coupling value k between them is greater than 0.35, and misaligned if k is less than or equal to 0.35, although this value would be application specific and could differ. Charger-to-IMD alignment is discussed prior to discussing charger-to-IMD centering.

Alignment is determined using measurements taken from sense coil 128, of which there is only one in the example of FIGS. 6A-6C. Sense coil 128 is referred to here as an "alignment" sense coil, in keeping with its function of determining alignment. However, as discussed further below, other sense coils may be used in the charging coil assembly 102 for different purposes.

As shown in FIG. 6B, the single alignment sense coil 128 is preferably a circle, and comprises a radius ra as measured from the center 150 of the charging coil 126. The charging coil 126 is likewise preferably circular, and in the example shown has a radius rp from center 150, such that the charging coil and the alignment sense coil are concentric. Radius rp can comprise the inside, outside, or average radius of the charging coil 126, which coil is depicted for simplicity in FIG. 6B and subsequent figures as just a single circle. It is preferred that radius ra be smaller than rp (e.g., that ra be between 50% to 100% of rp), as this is useful in determining a misalignment condition, as explained subsequently. However, this is not strictly necessary. Radius ra may also equal rp, or even be greater than rp. Further, charging and sense coils can take shapes other than circular (e.g., square, rectangular, or other shapes), although circular coils are described for simplicity. Note that even non-circular coils can share the same centers and hence be concentric.

Radii ra and rp are also preferably set in accordance with the size of the IMD 10 whose battery 14 is being charged. In this regard, the IMD 10 can be said to have a radius ri. Radius ri can be an estimate or average distance from a center 160 of the IMD 10. Center 160 can comprise a center or centroid of the charging coil 36 (FIGS. 1B and 1C) in the IMD 10, and may comprise the point that when perfectly aligned with the center 150 of the charging coil 126 (the charging coil assembly 102) provides a maximum coupling between the charging coils 126 and 36 in the charging coil assembly 102 and IMD 10 respectively, and hence the fastest charging of the IMD's battery 14. Radius ri can also comprise an average distance between center 160 and a significant boundary of the IMD 10, such as its charging coil 36 or its case 12 or a centroid of such boundary. Radii ra and rp are preferably larger than radius ri of the IMD 10, as this will allow the charging coil 126 to vary in position laterally from the IMD 10 while still keeping the IMD 10 fully bounded within the area of the charging coil 126. For example, it is preferred that radii ra and/or rp be at least twice the radius of ri.

As the charging coil 126 produces the magnetic field 66, some amount of the magnetic field 66 will couple to the alignment sense coil 128, with the degree of coupling being affected by position of the underlying IMD 10. This coupling causes a voltage Va to be formed across the alignment sense coil 128, which voltage will be smaller when the IMD 10 is generally bounded by the area of alignment sense coil 128. This is shown in the graph in FIG. 6B, which shows voltage Va as a function of radius r, where r comprises a radial offset between the charging coil 126 and the IMD 10, i.e., the distance between their centers 150 and 160. Voltage Va, like the magnetic field 66 and Vcoil, is AC in nature, and will have a frequency equal to that of the magnetic field 66 coupled to it.

Va can be discussed and is graphed in FIG. 6B in terms of its maximum magnitude Va+, such as its rms, zero-to-peak, or peak-to-peak value. As radius r increases from a perfectly centered condition (r=0), magnitude Va+ will increase slowly as the IMD 10 is still generally bounded by the alignment sense coil 128. When radius r increases such that the IMD 10 breaches the alignment sense coil 128, magnitude Va+ starts to increase more significantly. This increase is shown linearly in FIG. 6B for simplicity, but may be otherwise. As radius r increases further, the IMD 10 will eventually be fully outside of the alignment sense coil 128, at which point magnitude Va+ will be maximized and again constant, as the IMD 10 will have little effect on coupling to the alignment sense coil 128. Note that a more accurate graph of magnitude Va+ taken from experimental result is shown later in FIG. 14A.

Magnitude Va+ can be tailored by appropriate design of the alignment sense coil 128. In this regard, note that Vcoil can range between +/−50V or so. Va by contrast preferably varies in a range that is able to be handled by the sensing electronics in the electronics module 104, which is explained further below. For example, Va may preferably be set to vary between +/−1V. Setting magnitude Va+ can be achieved by varying the proximity of the alignment sense coil 128 to the charging coil 126, for example, by varying ra relative to rp. Magnitude Va+ can also be set by engineering the conductive traces in the circuit board 124 from which alignment sense coil 128 is built. For example, the thickness and/or width of the traces of alignment sense coil 128 can be varied, as can the number of turns that form the alignment sense coil 128. Magnitude Va+ will generally scale with the number of turns. Note that while circular sense coil 128 appears to comprise only a single trace comprising only a single turn in the figures for simplicity, the reality might be otherwise, and instead a multi-turn circle-shaped sense coil 128 can be formed in either single-level or multi-level trace circuit boards.

A magnitude alignment threshold, Va+(th), can be chosen from the relationship between Va+ and radius r. (A different threshold Vp+(th) shown in FIG. 6B is discussed later). In the example shown, Va+(th) can be determined as the point at which r=ra, i.e., when the center 160 of the IMD 10 is located at the sense coil 128. At this point, illustrated in FIG. 6C, the IMD 10 is roughly half inside and half outside of the sense coil 128 (and the charging coil 126). This is just an example however and experimentation and simulation can dictate choosing Va+(th) in different manners. For example, the alignment between the charging coil 126 and the IMD 10 in FIG. 6C may result in the IMD's charging coil 36 receiving too little of the magnetic field 66 as a practical matter. If so, a lower value for Va+(th) could be chosen which would indicate misalignment at a radius r smaller than ra.

Once a suitable magnitude alignment threshold Va+ (th) is determined, it may be used by position circuitry 140 to determine and indicate alignment and/or misalignment to the patient. As shown in FIG. 6A, AC signal Va as formed across alignment sense coil 128 is sent via cable 106 to the electronics module 104. Va in this example is digitized via an Analog-to-Digital converter 142, and presented to position circuitry 140. In position circuitry 140, magnitude Va+ may be determined, and how this can occur is explained later with respect to FIGS. 13A-13D. In any event, position circuitry 140 can digitally compare magnitude Va+ to magnitude alignment threshold Va+ (th) stored in or accessible to the position circuitry 140. Analog circuitry can be used as well, although this isn't shown. For example, an analog magnitude Va+, for example as produced by rectifier circuitry (not shown) could be compared to an analog magnitude alignment threshold Va+(th) at a comparator.

Regardless of how Va+ is sensed and compared to Va+ (th), the position circuitry 140 can issue an alignment indicator 74. For example, if Va+>Va+(th), the position circuitry 140 can issue a misalignment indicator 74, which can comprise issuing a sound from a speaker (a "beep"), issuing a notification on a display if the electronics module 104 has one, or illuminating one of the LEDs (e.g., 118*b*). Va+ may be compared to Va+(th) periodically as discussed in detail later, and measures of Va+ may be averaged to smooth out noise in the data. If the patient is able to move the charging coil housing 102 to achieve better alignment between the charging coil 126 and the IMD 10, the alignment indicator 74 can cease. Note that alignment indicator 74 can alert the patient to either an alignment condition, a misalignment condition, or both.

The magnitude alignment threshold Va+(th) may be chosen assuming an IMD 10 of medium depth d in a patient's tissue, and thus a medium distance between the charging coil 126 and the IMD 10. However, in actual use, a patient's IMD 10 may be more shallow or deeper than what is assumed, in which case Va+ would be decreased or increased respectively, as shown in dotted lines in FIG. 6B. A single unvarying magnitude alignment threshold Va+(th) used in position circuitry 140 may be sufficient to determine alignment for these different depths. On the other hand, a single Va+(th) may also be counter-indicated because it would not intersect curves where Va is increasing at all depths, or may not intersect the curves sufficiently near a desired radius (e.g., r=ra) to accurately establish a boundary between alignment and misalignment. Therefore, Va+(th) can be adjustable to raise Va+(th) for patients having deep implants and to lower Va+(th) for patients having shallow implants so that misalignment is appropriately indicated for both conditions. For example, the magnitude alignment threshold Va+(th) could be adjusted using the tuning process described in U.S. Pat. No. 9,227,075 discussed in the Background.

The voltage induced across the alignment sense coil 128, Va, will vary not only as a function of IMD 10 depth, but also in accordance with the power of the magnetic field 66 that is produced by the charging coil 126. This is important to recognize because the charging coil 126 and hence the power of the magnetic field 66 may be controlled and varied in the charging system 102 for any variety of reasons, some of which are discussed later. Such control will also affect Va, which may make comparison of magnitude Va+ to a set magnitude alignment threshold Va+(th) difficult. As such, it may be necessary for the position circuitry 140 to normalize the Va+ measurement with respect to the power of the magnetic field 66 before it is compared to the magnitude alignment threshold, Va+(th). Such normalization of the Va+ measurement can comprise for example dividing Va+ by any number of parameters that would indicate magnetic field strength. This could include the magnitude of the voltage across the charging coil 126 (Vcoil+), the magnitude of the current through the charging coil 126 (Icharge+), or inputs to the charging circuitry 64, such as a duty cycle at which the charging circuitry 64 drives the charging coil 126, as explained later. Instead of normalizing the sense coil measurement Va+, the threshold, Va+(th), could also be normalized (e.g., by multiplying it by a parameter indicative of indicate magnetic field strength).

Normalization of sense coil measurements though are not strictly necessary. For example, the charging coil 126 may be controlled to produce a test or default magnetic field 66 of a known constant power at times when sense coil measurements are taken to determine alignment, as discussed further below. Magnitude Va+ thus would not vary due to changes in magnetic field power at those times, allowing a magnitude alignment threshold Va+(th) to be chosen and applied with more confidence.

FIGS. 7A-7C show another example in which a single sense coil can be used to determine alignment. In this example, the alignment sense coil 128' comprises an edge detector coil, so named because the coil 128' is shaped to detect the presence of the IMD 10 when it generally breaches an area (A) bounded by two circular concentric pieces relative to center 150: an inner piece of smaller diameter ra1, and an outer piece of larger diameter ra2. Alignment sense coil 128' is circular and again is concentric with the charging coil 126. The inner and outer pieces are connected such that a current flowing through the alignment sense coil 128' will flow in different directions in the two pieces. For example, and as shown by the arrows in FIG. 7A, a current flowing clockwise in the smaller diameter piece (ra1) will flow counter-clockwise in the larger diameter piece (ra2). Ignoring the IMD 10 for a moment, notice that a magnetic field 66 passing though the pieces of the alignment sense coil 128' will induce currents in the two pieces that oppose one another because of the manner in which they are connected. In effect then, the total current flowing in the alignment sense coil 128', and the resulting voltage Va that forms across it, will be proportional to the difference in area between the outer and inner pieces, i.e., the area A bounded between them.

Like the first single alignment sense coil 128 of FIGS. 6A-6C, the radii of the inner (ra1) and outer (ra2) pieces are generally close to, but preferably smaller than, the radius rp of the charging coil 126. Further, radii ra1 and ra2 are preferably close in value (e.g., ra1 between 50% to 95% of ra2) to define a narrow area A. The average radius of the two pieces, and hence the alignment sense coil 128' generally, may be referred to as a single radius ra for simplicity. As with the alignment sense coil 128 described earlier, each of the inner and outer pieces of alignment sense coil 128' can be tailored in terms of their thicknesses, lengths, and numbers of turns, although this isn't illustrated. Again, modifying such variables is useful to tuning the range of Va. Alignment sense coil 128' is again preferably formed in the traces of circuit board 124, although that isn't strictly necessary.

When the charging coil 126 is perfectly aligned with the IMD 10 (i.e., when r=0, and centers 150 and 160 coincide), the IMD 10 doesn't eclipse the area A of the alignment sense coil 128'. The IMD 10 would thus have limited effect on the coupling of the magnetic field 66 to the alignment sense coil 128', and magnitude Va+ would be near a maximum value, as shown in FIG. 7A. As radius r increases, the IMD 10 will start to encroach upon area A of the alignment sense coil 128', and Va+ starts to decrease, eventually reaching a minimum when the IMD 10 is generally eclipsing the alignment sense coil 128' to a maximum extent—i.e., when r=ra. As r increases further, the IMD 10 would eventually start to move outside of area A, and Va+ would increase, eventually reaching a maximum value when the IMD 10 no longer affects coupling to the alignment sense coil 128'. Notice that magnitude Va+ at its maximum (high values of r) would be higher (Δ) than Va+ at low values (e.g., r=0), simply because at low values the IMD 10 will have some small coupling to the alignment sense coil 128'.

The minimum value of magnitude Va+ assists in choosing a magnitude alignment threshold Va+(th) that can be used by the position circuitry 140 when alignment sense coil 128' is used. While the magnitude alignment threshold Va+(th) may be set to the minimum value of Va+, Va+(th) may also be set at a value slightly higher than this minimum to ensure that it is not "missed" by the position circuitry 140. Thus, and as before, magnitude Va+ of alignment sense coil 128' can be sensed and used to indicate misalignment by comparison to alignment threshold Va+(th).

Position circuitry 140 may be modified to account for the difference in shape of the Va+ versus radius curve of FIG. 7A when determining misalignment. For example, position circuitry 140 may determine whether Va+ has fallen (e.g., to Va(th)), and subsequently starts to increase, and issue a misalignment indicator 74 at that time. Note in this regard that position circuitry 140 may store previous Va+ measurements as a function of time.

Use of the edge-detection alignment sense coil 128', and the shape of its Va+ curve versus radius, may allow for choosing of a magnitude alignment threshold Va+(th) that can accurately establish a boundary between alignment and misalignment regardless of IMD 10 depth. FIG. 7A shows two Va+ curves for deep and shallow implants. A single Va+(th) can be chosen that is above the minimum of Va+ for both of these extreme cases, hence allowing Va+ to be used to determine alignment regardless of implant depth, and potentially without the need to adjust Va(th) for different IMD depth conditions. That being said, Va+(th) can as before be adjusted for different IMD depths per U.S. Pat. No. 9,227,075 discussed earlier. Further, either Va+ or Va+(th) can be normalized to account for the power of the magnetic field 66, as discussed earlier.

Figure 8A:
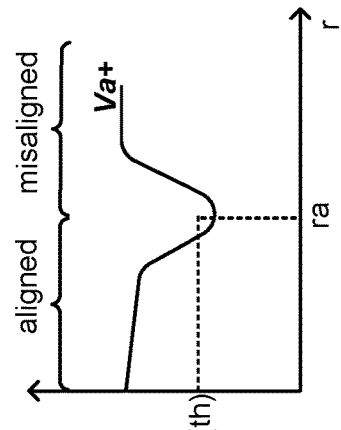
FIGS. 8A and 8B show use of a third alignment sense coil arrangement comprising two or more separate alignment sense coils in the charging coil assembly, as well as circuitry for detecting and indicating misalignment between the charging coil and the IMD, in accordance with an example of the invention.
Figure 8A:
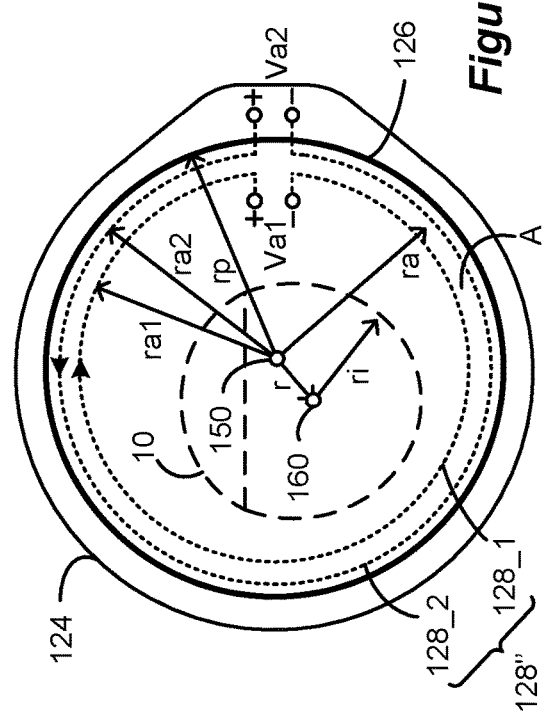
Figure 8B:
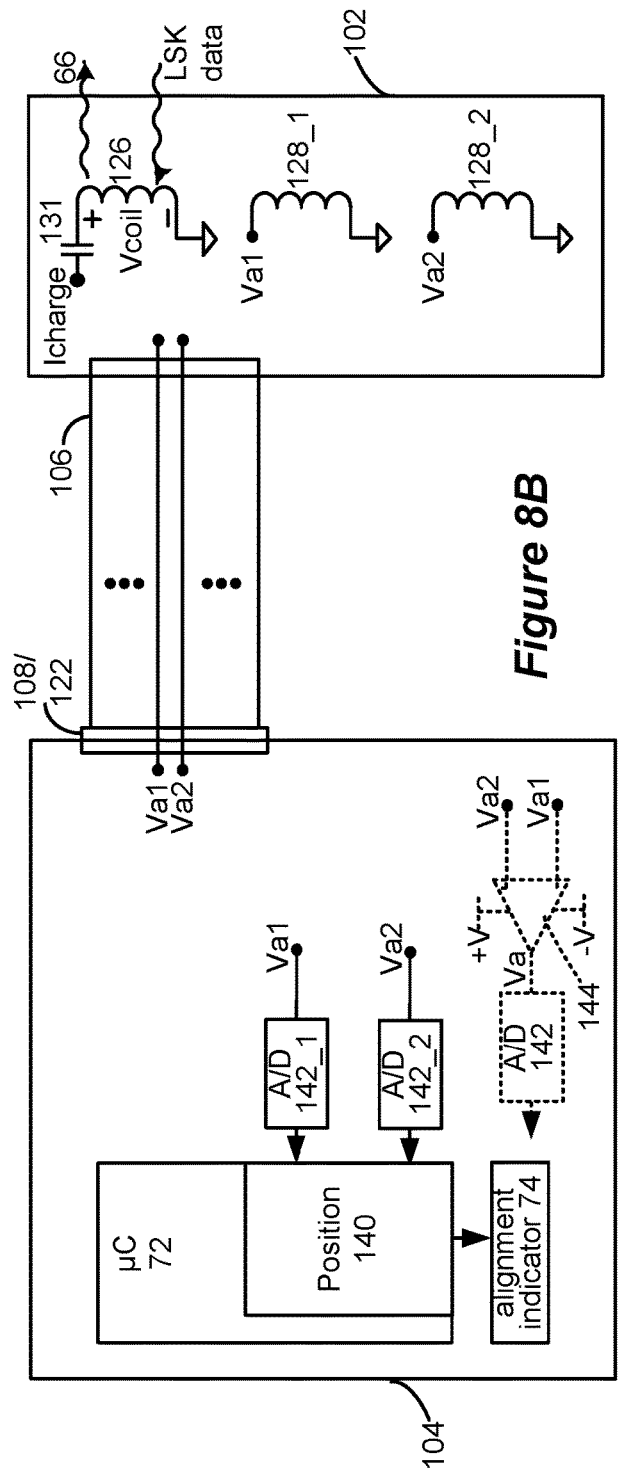

FIGS. 8A and 8B present another alignment sense coil arrangement 128" that is similar in function to the edge detection alignment sense coil 128' of FIGS. 7A-7C, but that uses concentric circular inner and outer alignment sense coils 128_1 and 128_2 that are not connected. As in alignment sense coil 128', inner and outer alignment sense coils 128_1 and 128_2 have radii ra1 and ra2 that are preferably close in value. However, because the alignment sense coils 128_1 and 128_2 are not connected, they will each be induced with individual voltages Va1 and Va2 that are passed to the electronics module 104 via cable 106. As before, each of alignment sense coils 128_1 and 128_2 can be tailored in terms of their geometry and number of turns to achieve values for Va1 and Va2 that appropriate for the electronics module 104.

At the electronics module 104, voltages Va1 and Va2 can be subtracted (or added if the voltages are of opposite polarity), which generally equals the singular voltage Va for the edge detection alignment sense coil 128' of FIGS. 7A-7C. Thus, the magnitude Va+ curve again experiences a minimum as shown in FIG. 8A, with an alignment threshold Va+(th) being established as already discussed. Processing of the sense voltages Va1 and Va2 can occur in position circuitry as before, with A/D 142_1 and 142_2 used to digitize these voltages, and with subtraction of them occurring in the position circuitry 140. Alternatively, both of voltages Va2 and Va1 can be presented to a differential amplifier 144 which can perform the subtraction prior to digitization and presentation to the position circuitry 140, as shown in dotted lines. Otherwise, the position circuitry 140 for alignment sense coil arrangement 128" (hereinafter alignment sense coil 128" for short, even though comprising two sense coils 128_1 and 128_2) can function as before to determine and indicate misalignment. A magnitude alignment threshold Va+(th) useable by position circuitry 140 can again be adjustable based on implant depth, and/or the position circuitry 140 can apply normalization to account for the power of the magnetic field 66, as explained previously.

While alignment sense coil 128" as shown comprises two alignment sense coils 128_1 and 128_2, note that even further numbers of alignment sense coils 128_x could be used, such as such as three or more. The inclusion of even further numbers of alignment sense coils 128_x would provide further information, and allow position circuitry 140 to determine alignment with further precision.

To this point, alignment sense coils 128, 128', and 128" have been described that determine misalignment between the charging coil 126 (charging coil assembly 102 more generally) and the IMD 10, i.e., when alignment is significantly poor such that the charging coil 126 and the IMD's charging coil 36 are not well coupled, and thus the charging coil 126 in its present position is unable to adequately charge the IMD's battery 14. However, in subsequent examples, charging system 100 uses one or more sense coils to determine whether the charging coil 126 is "centered" with respect to the IMD 10. As explained below, a charging coil 126 is "centered" with respect to the IMD 10 when it is well aligned with IMD 10, i.e., when the charging coil 126 and the IMD's charging coil 36 are very well coupled, and thus the charging coil 126 is able to quickly charge the IMD's battery 14. For example, the charging coil 126 can be said to be centered with the IMD 10 if the coupling value k between them is greater than 0.65, and not centered if k is less than or equal to 0.65, although again this value would be application specific. A charging coil 126 can thus be aligned (not misaligned) with the IMD 10 even if it is not centered, e.g., if $0.35 < k \leq 0.65$).

Figure 9A:
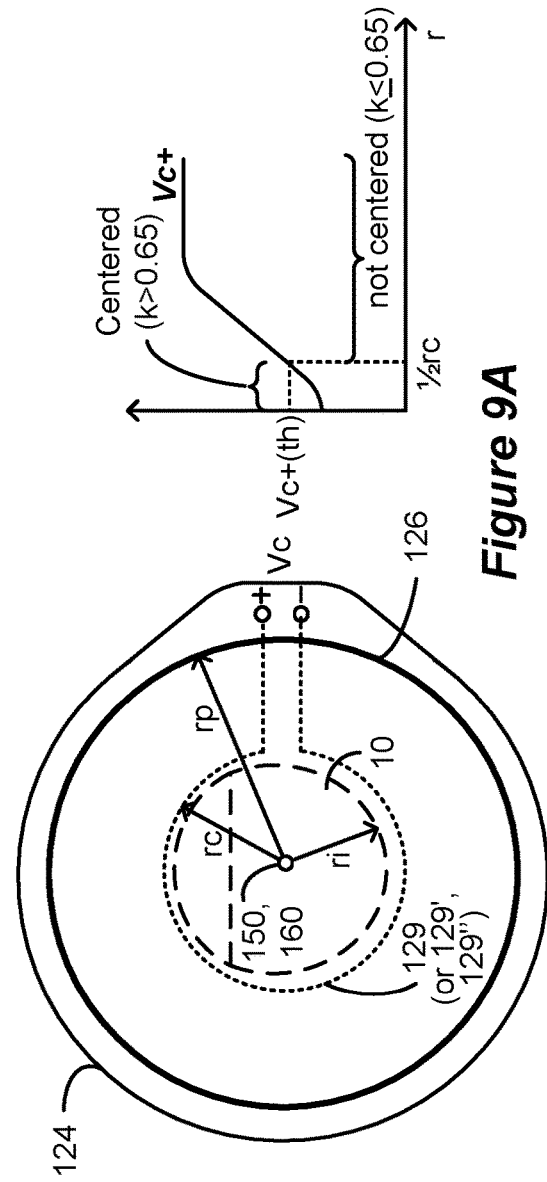
FIGS. 9A-9C show use of a centering sense coil in the charging coil assembly, as well as circuitry for detecting and indicating a non-centered condition between the charging coil and the IMD, in accordance with an example of the invention.
Figure 9C:
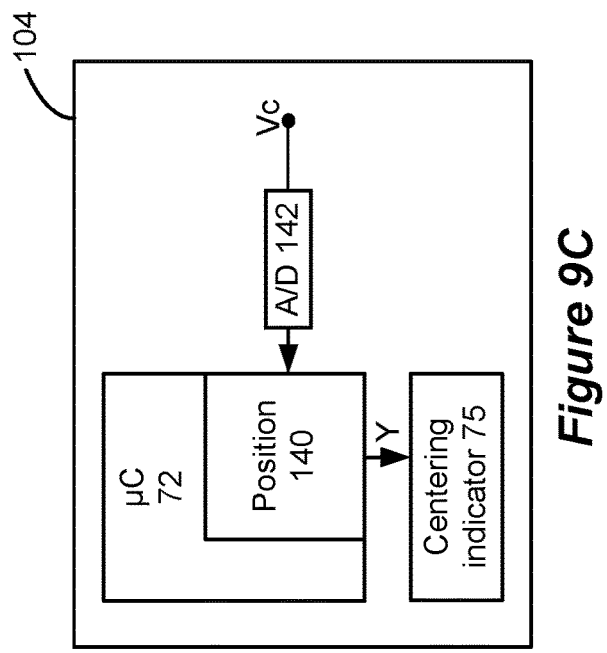
Figure 9B:
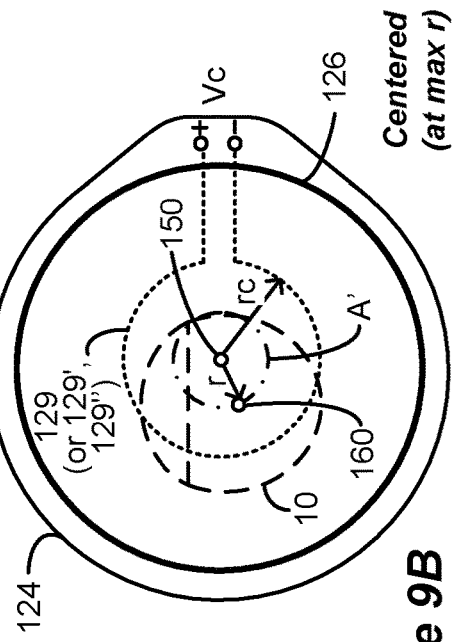

To detect when the charging coil assembly 102 is centered with the IMD 10, circuit board 124 can include one or more centering sense coils 129, shown first in FIGS. 9A-9C. In the example shown, centering sense coil 129 is circular, similar to the alignment sense coil 128 of FIGS. 6A-6C, but sense coil 129 could also comprise an edge detector centering sense coil (129') that would be similar in geometry to the edge detector alignment sense coil 128' illustrated earlier in FIGS. 7A-7C. Sense coil 129 could also comprise one or more separate centering sense coils (129_1 and 129_2; collectively 129") that would be similar in geometry to the alignment sense coil 128" illustrated earlier in FIGS. 8A and 8B. Centering sense coil is for simplicity subsequently referred to by element 129, even though alternative non-illustrated geometries 129' or 129" could also be used.

Like the alignment sense coils, centering sense coil 129 is induced with a voltage, Vc (or Vc1 and Vc2 if two or more separate centering sense coils are used per 129"). Like Va, the maximum magnitude of Vc, Vc+ is a function of the coupling to the primary charging coil 126 and coupling related to the proximity of the IMD 10. Thus, magnitude Vc+ will drop when the IMD 10 is proximate to the area encompassed by the centering sense coil 129. Centering sense coil 129 may again be formed in the conductive traces of the circuit board 124 but could also comprise wire windings, and the geometry of the sense coil 129 can be tailored to achieve values for Vc (or Vc1 and Vc2) that can be handled by the electronics module 104.

Like the alignment sense coil 128, centering sense coil 129 is preferably centered around center 150, and comprises a radius rc (or radii rc1 and rc2 with an average radius of rc if 129' or 129" are used). In one example, radius rc can be approximately equal to radius ri of the IMD 10. As shown in the graph of magnitude Vc+ versus radius r, which shows Vc+ for a single sense coil like that of FIG. 6B earlier, Vc+ will be at a minimum when the charging coil 126 (charging coil assembly 102) is perfectly aligned with the underlying IMD 10 (i.e., when centers 150 and 160 coincide, and r=0). As radius r increases, the IMD 10 will start to breach the extent of the centering sense coil 129 almost immediately, and thus Vc+ will start to increase, and will eventually come to a maximum value when the IMD 10 is no longer coupled to the centering sense coil 129. From this graph, a magnitude centering threshold, Vc+ (th) can be chosen. Like the magnitude alignment threshold Va+(th) discussed earlier, Vc+ (th) can be chosen in different manners. In the example shown, Vc+ (th) is chosen to establish that the charging coil 126 is centered with respect to the IMD 10 if the radius r between the two is less than ½rc. Thus, the charging coil assembly 102 will be deemed centered to the IMD 10 so long as the center 160 of the IMD 10 is within a small area A' relative to the center 150 of the charging coil 126, as shown in FIG. 9B.

Positioning circuitry 140 can then compare magnitude Vc+ as measured to Vc+ (th) and issue a centering indication 75. For example, if the charging coil 126 is not centered—i.e., if Vc>Vc(th)—then a centering indicator 75 may issue, which like the alignment indicator 74 may comprise use of a speaker, LEDs, etc. Centering indicator 75 can alert the patient to either a centered condition, a non-centered condition, or both. Notice also that the sensing circuitry for Vc (e.g., A/D converter 142) can also be the same or similar to the circuitry used to sense Va.

Similar to the magnitude alignment threshold Va+(th), the centering threshold Vc+ (th) could also be adjusted for individual patients based upon the particular depth of their IMDs 10, and/or the position circuitry 140 can apply normalization to account for the power of the magnetic field 66, as described above.

To this point, alignment (FIGS. 6A-8B) and centering (FIGS. 9A-9C) of the charging coil 126 to the IMD 10 have been discussed separately. However, there are additional advantages to IMD 10 charging when both techniques are used together, as shown in FIGS. 10A-11B. In particular, using both techniques together allows the charging system 100 to determine and/or indicate three possible positions of the charging coil 126 relative to the IMD 10: centered (e.g., $r<\frac{1}{2}rc$ or $k>0.65$), misaligned (e.g., $r>ra$ or $k\leq 0.35$), and a middle position of intermediate coupling in which the charging coil 126 is not centered but is not misaligned with the IMD ($\frac{1}{2}rc<r<ra$ or $0.35<k\leq 0.65$).

Figure 10A:
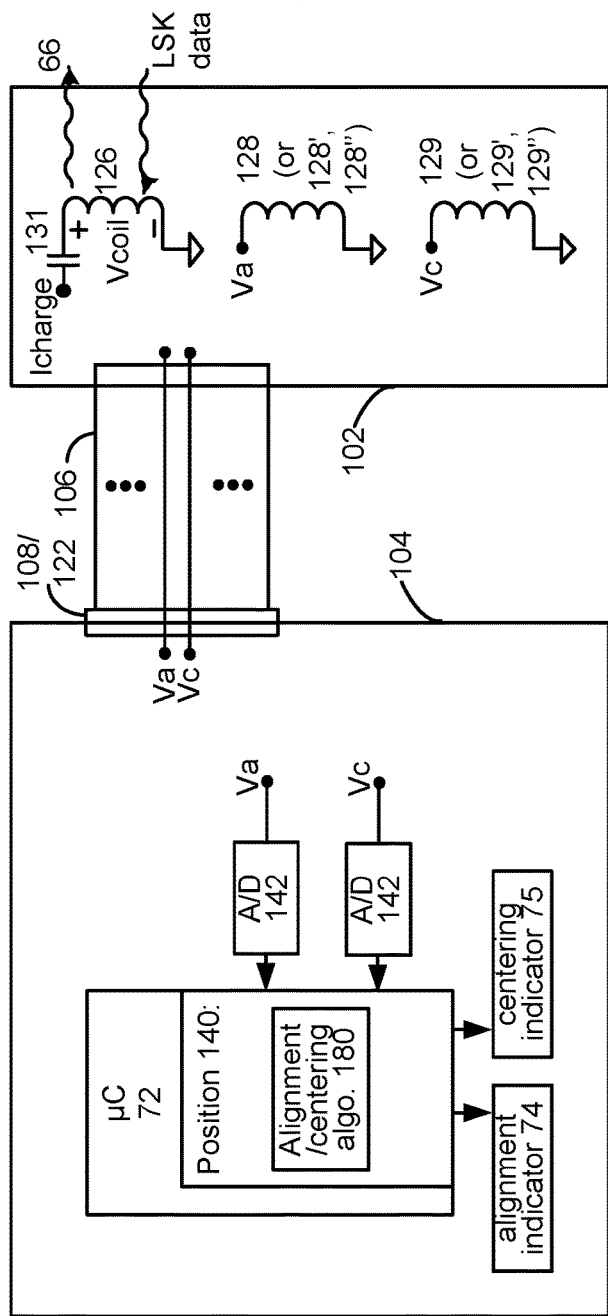
FIGS. 10A and 10B show use of both an alignment sense coil and a centering sense coil in the charging coil assembly, as well as circuitry for detecting and indicating misalignment and/or non-centered conditions between the charging coil and the IMD, in accordance with an example of the invention.
Figure 10B:
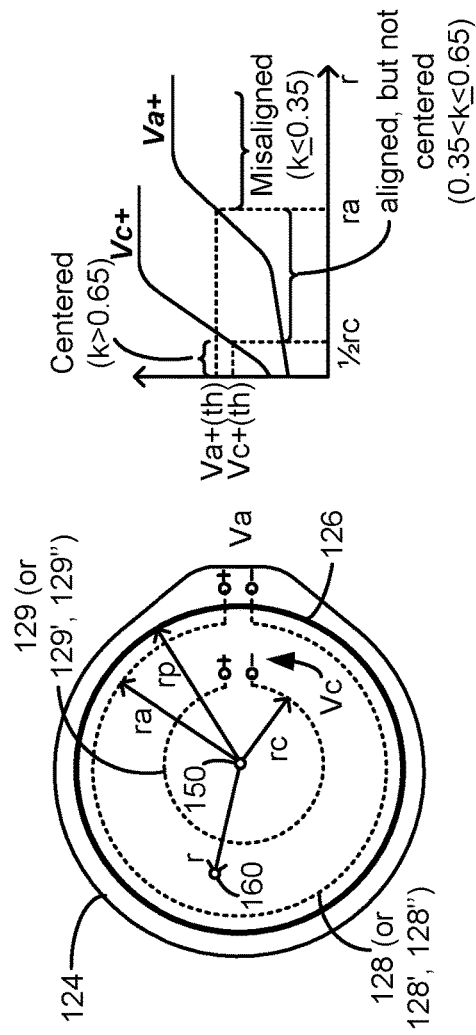
Figure 11A:
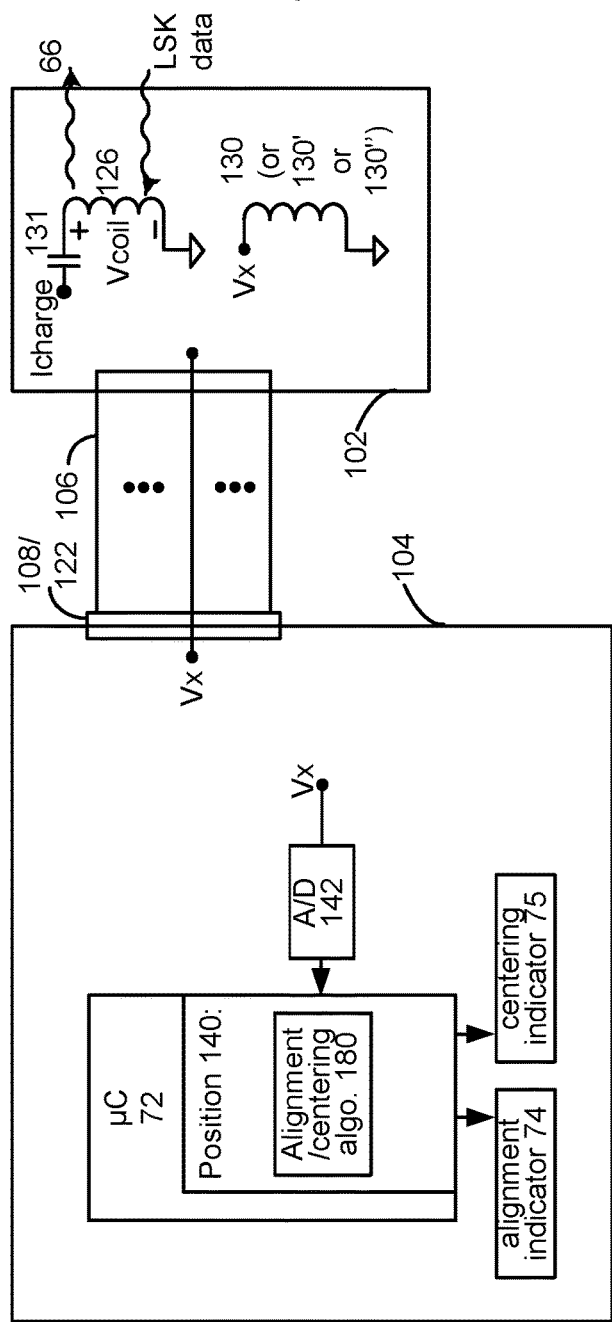
FIGS. 11A and 11B show use of a single alignment/centering sense coil in the charging coil assembly, as well as circuitry for detecting and indicating misalignment and/or non-centered conditions between the charging coil and the IMD, in accordance with an example of the invention.
Figure 11B:
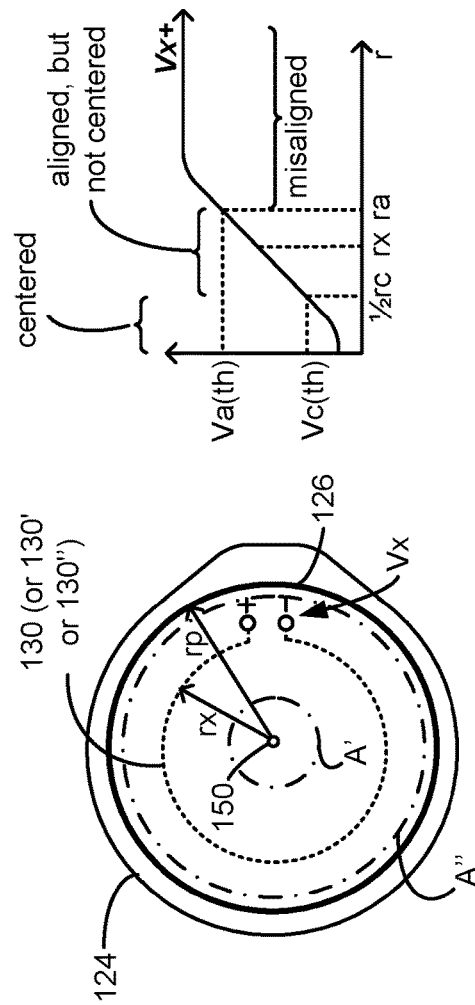

Starting with FIGS. 10A and 10B, the charging coil assembly 102, in addition to charging coil 126, includes both an alignment sense coil 128 and a centering sense coil 129, which can be constructed in any of the various forms described earlier. Single coils 128 and 129 of radii ra and rc (see FIGS. 6B and 9A) are illustrated for simplicity.

Figure 12A:
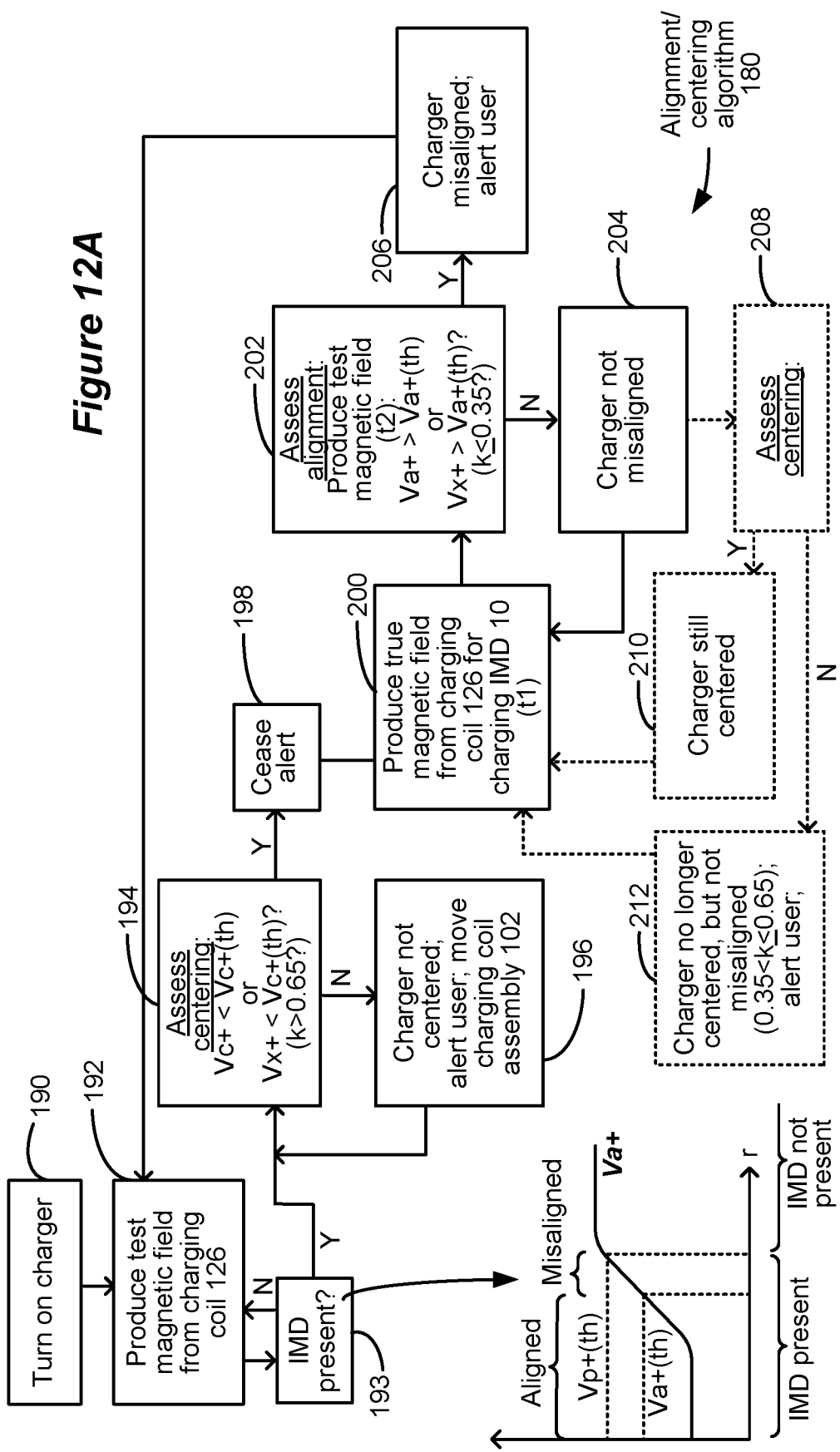
Figure 12B:
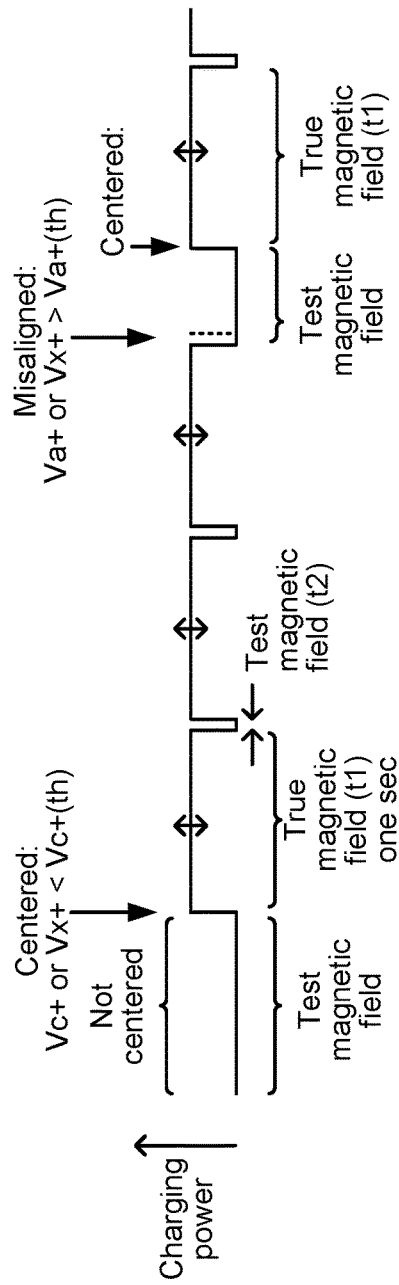
FIG. 12B shows the magnetic field produced via the algorithm, in accordance with an example of the invention.

The position circuitry 140 is programmed an alignment and centering algorithm 180, which is discussed further with reference to FIGS. 12A and 12B. The algorithm 180 receives Va and Vc as digitized, and compares magnitudes Va+ and Vc+ to thresholds Va+(th) and Vc+ (th) as before to determine whether the charging coil 126 is centered, misaligned, or not centered but not misaligned. Either or both of an alignment indicator 74 and/or centering indicator 75 can issue accordingly. One skilled will realize that algorithm 180 can be stored on any non-transitory computer readable media, including solid state memory within the control circuitry 72.

One advantage of using separate alignment 128 and centering 129 sense coils—or two different concentric coils more generally—concerns normalization of the sense coil measurements. Va and Vc will vary with the power of the magnetic field 66 produced by the charging coil 126, and as discussed above such measurements can be normalized to remove magnetic field power as a variable, and to make comparison to thresholds Va+(th) and Vc+ (th) more reliable. However, when two or more sense coils are used, one sense coil measurement can be normalized using the other measurement, because that other measurement will be generally indicative of magnetic field strength (even if affected by IMD coupling). For example, magnitude Va+ can be divided by magnitude Vc+ before it is compared to magnitude alignment threshold Va+(th), and Vc+ can be divided by Va+ before it is compared to centering threshold Vc+ (th).

In fact, an additional sense coil can be included in the charging coil assembly 102 and measured merely for normalization purposes. For example, in FIG. 10B, sense coil 128 and its measured voltage Va may not necessarily be used in an alignment determination. Instead, centering and/or alignment might be determined by sense coil 129 and its voltage Vc (as explained further with respect to FIGS. 11A and 11B), with Va+ merely used to normalize Vc+ (e.g., Vc+/Va+) before it is compared to a relevant threshold (Va+(th) and/or Vc+ (th)).

Alignment and centering can also be detected using a single sense coil. For example, in FIGS. 11A and 11B, a single alignment/centering sense coil 130 is used. In the example shown, alignment/centering sense coil 130 is circular, although it could comprise an edge detector sense coil (130') or separate centering sense coils (130_1 and 130_2; collectively 130"), similar to those shown in FIGS. 7A-8B. Alignment/centering sense coil is for simplicity subsequently referred to by element 130, even though alternative non-illustrated geometries 130' or 130" could also be used.

The radius rx of the alignment/centering sense coil 130 is preferably between the radii ra and rc of individual alignment and centering coils 128 and 129 described earlier. A magnitude of voltage Vx induced across the coil 130, Vx+, can be compared to separate magnitude thresholds Va+(th) and Vc+ (th) in the alignment and centering algorithm 180 of the position circuitry 140. Such thresholds can be chosen to establish boundaries for a centered condition (within area A') and a misaligned condition (outside area A") for the charging coil 126 relative to the IMD 10. Such boundaries may coincide with or be established in light of the radii of the individual alignment and centering coils 128 and 129 presented earlier. For example, alignment magnitude threshold Va+(th) may establish a radius of ra outside of which the IMD 10 is deemed misaligned (i.e., when Vx+>Va+(th)), while centering magnitude threshold Vc+ (th) may establish a radius ½Vc inside of which the IMD is deemed centered (when Vx+<Vc+ (th)). Alignment and centering indicators 74 and 75 can again be used to indicate centered, misaligned, and/or aligned but not centered conditions.

An example of alignment and centering algorithm 180 is summarized briefly before being explained in detail with respect to FIGS. 12A and 12B. The algorithm 180 requires a patient at the beginning of an IMD charging session to first center the charging coil 126 (charging coil assembly 102) with the underlying IMD 10 (e.g., $r<\frac{1}{2}rc$). Thereafter and during charging, the charging coil 126 may move, and may even move from a non-centered position (e.g., $r>\frac{1}{2}rc$) so long as the charging coil 126 is still aligned with the IMD 10 (e.g., $r<ra$). However, should the charging coil 126 move to such an extent that it is no longer aligned with the IMD 10 (e.g., $r>ra$), then the patient will be required to once again re-center the charging coil assembly 102 (e.g., $r<\frac{1}{2}rc$) before charging will again commence in earnest.

Such operation of the alignment and centering algorithm 180 is beneficial, because it ensures, initially and later after misalignment, that the charging coil 126 is centered with the IMD 10, and thus that the two are very well coupled. Requiring such centered positioning means that the charging coil 126 is not likely to soon move out of alignment with the IMD 10, because it would have to move an appreciable distance (from ½rc to ra) to do so.

Figure 4B:
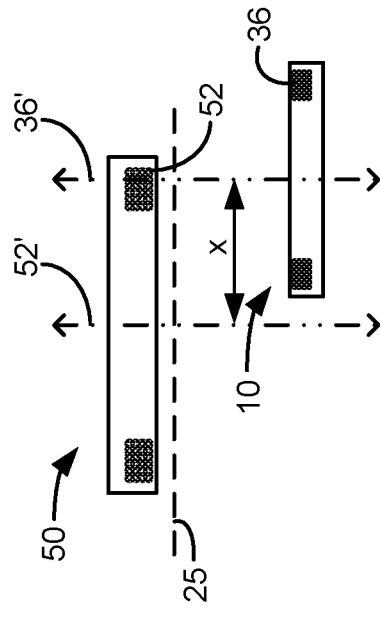
FIGS. 4A-4C show various position between an external charger and an IMD that can affect their coupling, in accordance with the prior art.
Figure 4C:
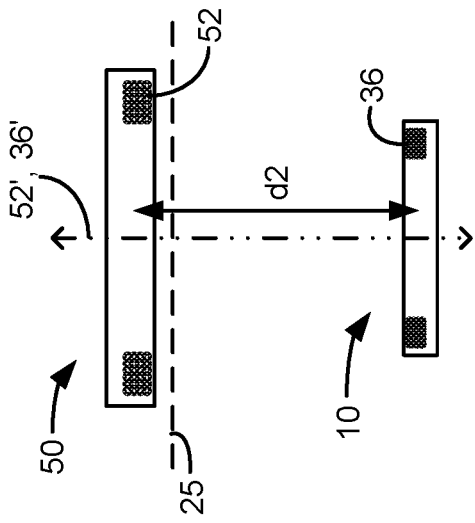
Figure 4A:
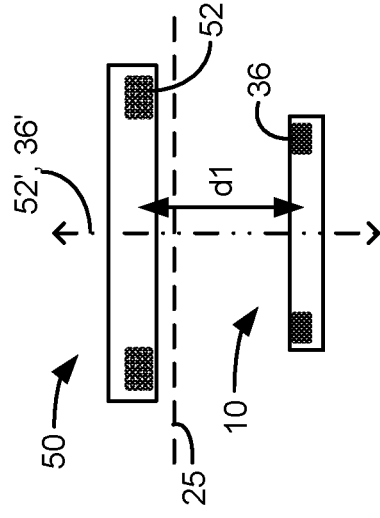

This is an improvement over previous alignment techniques in which charger-to-IMD positioning was merely assessed by a simple aligned/misaligned determination. Consider for example FIG. 3, in which alignment was determined (70) by merely comparing Vcoil of the primary coil 52 to an alignment threshold Vt. Assume at the beginning of a charging session that the external charger 50 is relatively poorly aligned with the IMD 10, perhaps because it is significantly offset (x) as shown in FIG. 4B. Assume further that the external charger 50 is nonetheless still technically aligned, because Vcoil<Vt, although Vcoil is also very close to Vt. The external charger 50 could easily soon go out of alignment (Vcoil>Vt) as the patient moves. This provides a frustrating use model for the patient, who believes his external charger 50 is aligned, only to find out a short time later (perhaps seconds later) that alignment requires his attention. Even thereafter should the patient move the external charger 50 back into alignment with the IMD 10 (Vcoil<Vt), the charger could again go quickly out of alignment with the IMD if again it is on the verge of being misaligned.

The alignment and centering algorithm 180 addresses this problem, because charging can't commence if the charging coil assembly 102 is only barely aligned with the IMD 10. Instead, the charging coil assembly 102 must then be centered with the IMD 10, in effect requiring the very good alignment with the IMD 10 that centering provides.

FIG. 12A shows alignment and centering algorithm 180 in flow chart form, while FIG. 12B shows the magnetic field that is produced at the charging coil 126 as a result of the algorithm. First, the patient turns on the charger system 100 (190), for example by pressing the on/off button 116 (FIG. 5B) on the housing 105 of the electronics module 104. A test or default magnetic field can then be produced from the charging coil 126 (192). As alluded to earlier, this test magnetic field 66 may be of a known constant power, and may be lower in power that a true magnetic field 66 used later in the process to operatively charge the IMD's battery 14. Use of a low-power magnetic field is preferred to ensure that the IMD 10 is not over-powered before the charging system 100 is able to determine whether the charging coil 126 is centered. A constant power test magnetic field by using a set duty cycle with the charging circuitry 64, as described in detail later.

The algorithm 180 may deduce as a first step whether the IMD 10 is present (193)—whether the charging system 100 detects the presence of the IMD 10 such that assessment of position and charging can begin. Detecting the presence of the IMD 10 can occur in any number of ways. For example, the magnitude of the voltage formed across the charging coil 126, Vcoil+, can be assessed during production of the test magnetic field, and compared to a IMD presence magnitude threshold, Vp+(th).

Alternatively, the charging system 100 may determine IMD presence using measurements taken from any of the sense coils illustrated earlier, and used later during the algorithm 180 to determine charger-to-IMD alignment and/or centering. For example, the bottom of FIG. 12A shows a graph of magnitude Va+ as measured at an alignment sense coil 128 (see FIG. 6B). In addition to assessment of the alignment magnitude threshold Va+(th) discussed earlier, Va+ may be compared to an IMD presence threshold Vp+(th), which may be set just below Va+'s maximum value. If Va+>Vp+(th), then the charging system 100 (e.g., position circuitry 140) may determine that the IMD 10 is not yet within a detectable range of the charging coil 126 (charging coil assembly 102). Although not illustrated, the detected presence or not of the IMD 10 may be indicated to the user through an alert issued by the charging system's user interface (e.g., one or more of LEDs 118a or 118b). Notice therefore that the charging system 100, in addition to determining alignment and misalignment, and/or centered and non-centered (conditions where the IMD 10 is present with respect to the charging coil 126), may additionally determine that the IMD 10 is not present with respect to the charging coil 126.

Still other techniques can be used to determine IMD 10 presence with respect to the charging coil 126 at step 193. For example, the technique of U.S. Pat. No. 9,186,520 can be used, which technique can also be used to automatically turn on the charging system when IMD 10 presence is detected.

Once IMD presence is determined and with the test magnetic field 66 produced, one or more voltages are sensed to determine whether the charging coil 126 is centered with the IMD 10 (194). For example, magnitude Vc+ of centering sense coil 129, or Vx+ of alignment/centering sense coil 130, perhaps as normalized in the various ways described earlier, can be compared to the centering threshold, Vc+ (th). Initially, it might be expected that the charging coil 126 is not well centered, especially if the patient is in the process of placing the charging coil assembly 102 proximate to the IMD 10. In that case, the patient would be alerted (centering indication 75) that the charging coil 126 is not centered (196) so that he can attempt to move the charging coil assembly 102 into a better position relative to the IMD 10. Such alert could be in the various forms previously described. In a particular example, such alert could comprise illuminating an LED (e.g., 118b) on the electronics module 104 with a color indicative of centering/alignment status. For example, LED 118b might initially be lit red before the charging coil 126 is centered.

The assessment of centering (194) can be repeated at sensible intervals, such as every 1.0 seconds or so. Once centering is achieved—for example, when Vc+ or Vx+<Vc (th) and thus the radius r between the charging coil 126 and the IMD 10 is less than ½rc as discussed in previous examples—the previously issued non-centered alert can cease (198). For example, LED 118b might now be lit green to indicate that the charging coil 126 is centered. Further, the charging coil 126 can now produce a true magnetic field 66 operable to charge the IMD 10's battery 14 (200). Such true magnetic field 66 is likely be higher in power than the test magnetic field, and may also vary per normal charging coil 126 operation and control, as shown by the arrows in FIG. 12B, and as discussed further subsequently. The true magnetic field 66 can continue to be produced for a reasonable time period (t1) such as 30 second or so.

Thereafter, the alignment and centering algorithm 180 will measure the alignment of the charging coil assembly 102 with respect to the IMD 10 (202). This measurement may again involve use of the constant low-power test magnetic field. Preferably, the alignment measurement takes place quickly, for example, over a period (t2) of 1.0 seconds, and thus doesn't significantly interrupt charging of the IMD 10 via the true magnetic field. Misalignment can be determined by assessing the magnitude Va+ of the sense coil 128 or magnitude Vx+ of alignment/centering sense coil 130, perhaps as normalized in the various ways described earlier.

If the charging coil 126 is not misaligned (204)—for example if Va+ or Vx+is <Va+(th) and thus the radius r is less than ra as discussed in previous examples—then charging can then continue (200), with the charging coil 126 once again producing a true magnetic field for another period t1. Note in this example that the charging coil 126 may no longer be centered with the IMD 10 at this point. That is, radius r may be greater than ½rc but less than ra. But in this example, that does not matter: so long as there is not a more-significant misalignment condition and thus the IMD 10 is still reasonably coupled to the charging coil 126 and adequately charged by it, charging via the true magnetic field can continue.

If the charging coil 126 is misaligned (206)—for example if Va+ or Vx+is >Va+(th) and thus the radius r is greater than ra—then the patient is again alerted (alignment indicator 74), such as by lighting the LED 118b red once again. The algorithm 180 then essentially returns to its beginning: a test magnetic field is produced from the charging coil (192), and once again the patient must move the charging coil assembly 102 to center it with the IMD 10 (e.g., r<½rc) (194-198) before a true magnetic field can begin again (200).

As just discussed, it may not matter to the alignment and charging algorithm 180 that the charging coil 126 eventually becomes non-centered with the IMD 10, so long as it also remains aligned (202-206). Normal charging of the IMD 10 can continue. However, optional steps in algorithm 180 shown in dotted lines can also be used to notify the user of the non-centered but aligned condition, even if it doesn't affect charging. If the charging coil 126 is not misaligned (204), the algorithm 180 can nonetheless check whether it is still centered (208), similar to what occurs initially in step 194. If the still-aligned charging coil 126 is still centered (210), charging can continue. In this circumstance, LED 118b can remain green (or can be turned to green if previously lit to amber, as explained momentarily). However, if the still-aligned charging coil 126 is not centered (212), the user may be alerted of this fact, even though charging will still continue, and even if the patient is not now required to move the charging coil 102. For, example, LED 118b might be lit amber in this circumstance. In effect, these optional steps in the algorithm 180 measure three different conditions for the charging system, and issue three different alerts: a centered condition (green), a non-centered but not misaligned condition (amber), and a misaligned condition (red).

It should be noted that steps 202 and 208—assessing alignment and centering—need not occur in the order illustrated and could be assessed concurrently. For example, it may be sensible to assess alignment (202) only if the charging coil 126 has become not centered (208).

Although the alignment and centering algorithm 180 is described using "test" and "true" magnetic fields 66 which may be different, this is not strictly necessary. Instead, the charging coil 126 may produce a single true magnetic field 66 through operation of the entire algorithm 180 of the type used to meaningfully provide power to the IMD 10. Normalizing of the sense coil measurement may become more important in this circumstance to account for possible variations in magnetic field 66 power, as discussed earlier.

To this point in the disclosure, charger-to-IMD position (e.g., alignment and/or centering) has been determined with reference to the maximum magnitude of the voltage that is induced on the sense coil. However, the inventors realize that other sense coil parameters may be used to determine charger-to-IMD positioning, in particular the phase angle (θ) of induced voltage relative to the signal used to drive the charging coil 126, and the resonant frequency (f(res)) of the charger/IMD system. The inventors realize further that use of two or more sense coil parameters—for example, two or more of magnitude, phase angle (θ), and resonant frequency f(res)—can be used to improve the positioning determination, in particular by allowing charger-to-IMD depth (d) to be determined as well as charger-to-IMD radius (r). Before discussing such concepts in detail, further details of the circuitry in the charger system 100 are discussed with reference to FIGS. 13A-13C.

FIG. 13A shows further details regarding the charging circuitry 64 used to energize the charging coil 126 with AC current, Icharge. A digital drive signal D is formed by a square wave generator 65, which may comprise a part of the control circuitry 72. Drive signal D comprises a pulse-width modulated (PWM) signal with a periodically-repeating portion that is high (logic '1') for a time portion 'a' and low for a time portion 'b'. As such, the drive signal D has a duty cycle DC equal to a/(a+b). Further, the drive signal D has a frequency f equal to 1/(a+b). The frequency f of the drive signal is generally set to or near the resonant frequency of the capacitor 131/charging coil 126 LC circuit (e.g., around 80 kHz), although the frequency of the drive signal can also be adjusted, as explained subsequently.

Charging circuitry 64 can comprise a well-known H-bridge configuration, including two N-channel transistors coupled to a power supply voltage Vcc, and two P-channel transistors coupled to a reference potential such as ground (GND). The transistors are driven on and off by the drive signal D and its logical complement D*. In so doing, the power supply voltage Vcc and ground are made to alternate across the LC circuit t frequency f, thus producing the magnetic charging field 66 at this frequency. Power supply voltage Vcc may comprise the voltage of the battery 110 (FIG. 5A) in the electronics module 104, or may be regulated from that voltage. As is well known, the duty cycle DC of the drive signal D can be increased from 0 to 50% to increase Icharge, thus setting the power at which the charging coil 126 is energized and hence the power of the resulting magnetic field 66.

The AC voltage Vy (e.g., any of Va, Vc, or Vx introduced earlier) induced across the sense coil 178 (e.g., any of 128, 128', 128'', 129, 129', 129'', 130, 130' or 130'' introduced earlier) will also have a frequency equal to f, but may be shifted in phase angle (θ) relative to the drive signal D (and hence relative to the voltage Vcoil across the charging coil 126 and the magnetic field 66). This is shown in FIG. 13B, in which phase angle θ is measured as the difference between the center of the drive signal D (top portion 'a') and where Vy=0. However, this is arbitrary, and phase angle θ of sense coil voltage Vy can be determined with respect to different reference points, or with respect to Vcoil or the magnetic field 66.

Sense coil voltage Vy is digitized at A/D 142 as mentioned earlier, and is sampled at a frequency, Fs. As shown, the digitized samples are provided to Vy magnitude and phase angle determination module 170, which may operate as firmware within the position circuitry 140 and within control circuitry 72 more generally. Module 170 is capable of concurrently determining both the magnitude of Vy (Vy+) and the phase angle (θ) by assessing N digitized samples of Vy. FIG. 13C explains the mathematics involved. Essentially, each of the samples ($Vy_N$) is multiplied by orthogonal trigonometric functions ($\sin(\omega \times t_N)$ or $\cos(\omega \times t_N N)$), added together, and normalized by the number of samples (1/N), rendering values I and R. The magnitude of Vy (Vy+) and phase angle (θ) are then determined as a function of I and R as shown in the equations at the right. Note that magnitude Vy+ determined in this manner comprises a zero-to-peak value of Vy, as shown in FIG. 13B.

Magnitude Vy+ and phase angle θ could also be determined in different manners as one skilled will understand, and need not be determined concurrently in the same module or circuitry. For example, magnitude Vy+ can be determined by rectifying Vy to a DC voltage, for example, using a full wave rectifier. Phase angle θ can also be determined using analog components. FIG. 13D for example shows that the phase angle between Vy and drive signal D can be determined using a phase comparator 182, which as is known outputs a voltage (Vcntr) that is indicative of the phase angle θ. If necessary, sensed voltage Vy can be limited (clipped) and level shifted into a digital signal that is more easily compared to the digital drive signal D at the phase detector 182.

It should be noted that the number of samples of Vy (N) and the frequency at which such samples are taken (Fs) can vary depending on the desired accuracy Vy+ and θ, and how long the measurement should take.

Another sense coil parameter that may be assessed to determine charger-to-IMD positioning is the resonant frequency, f(res), of the charger-IMD system. The resonant frequency f(res) can be determined in a resonant frequency determination module 172 (FIG. 13A) within the position circuitry 140, which also can be operable as firmware. Module 172 may use the phase angle θ determined in module 170 to assist in determining the resonant frequency, f(res). Specifically, module 172 may vary the frequency f of the drive signal D until the phase angle θ received from module 170 equals 0, thus establishing f(res) at that frequency f Such varying of the frequency can be an iterative process, and may require several adjustments to the frequency of the drive signal D. How the frequency is adjusted may involve consideration of the polarity of the phase angle θ. For example, module 172 may lower the frequency f if the phase angle is positive and raise it if the phase angle is negative.

Frequency adjustment to the drive signal D to determine resonant frequency f(res) may occur by varying either or both of time portions 'a' and 'b' at the square wave generator 65. In one example, both of time portions 'a' and 'b' may be equally scaled, thus keeping the duty cycle DC of the drive signal D constant, and thus keeping the power of the charging coil 126 and magnetic field 66 constant. However, this is not strictly necessary, as variations in duty cycle and power resulting from small frequency adjustments may be negligible or permissible. Thus, only portions 'a' or 'b' may be varied.

Measuring f(res) of the charger-IMD system may also be accomplished using analog circuitry. Referring again to FIG. 13D, the determined phase angle (expressed as Vcntr) may be compared to a reference voltage (Vref) at a comparator 186. Vref may be set to equal Vcntr when the phase angle is zero degrees, and thus the comparator may output a digital signal to the square wave generator 65 indicating whether the phase angle is higher ('1') or lower ('0') than zero degrees. The square wave generator 65 in turn may thus increase or decrease the frequency of the drive signal D, which is provided back to the phase comparator 182 via feedback loop 190 until Vcntr=Vref and phase angle θ equal zero, at which point f(res) is determined as the frequency f to which the drive signal D has been adjusted. Still other analog feedback circuits could be used as well, such as phase- or delay-locked loops.

FIG. 14A shows experimental results of how the parameters of magnitude Vy+ (upper left), phase angle θ (upper right), and resonant frequency f(res) (lower left) as measured from the sense coil 178 vary as a function of radial offset r and depth d between centers 150 and 160 of the charging coil 126 and the IMD 10 respectively. FIG. 14B shows this same data, but graphed for each sense coil parameter at a constant depth (d=10 mm), which represents a typical depth at which the charging coil assembly 102 and the IMD 10 would be separated when the IMD 10 is implanted in a patient. In this experiment, the radius rp of the charging coil 126 was about 30 mm, and the radius of the sense coil 178 (in this example, a circle; see, e.g. FIG. 11B) was about 15-20 mm.

FIG. 14B verifies that any of sense coil parameters magnitude Vy+, phase angle θ, or resonant frequency f(res) can be measured and assessed alone to determine charger-to-IMD positioning—such as alignment or centering as discussed earlier. For example, and as discussed earlier with reference to FIG. 6B for example, a magnitude threshold Vy+(th) can be stored in a database 200 associated with position circuitry 140 (FIG. 13A) and compared to magnitude Vy+ as measured (module 170) to determine charging coil 126 positioning. As the data shows, a magnitude threshold Vy+(th)=0.18 V establishes a charger-to-IMD radius r of about 27 mm at the indicated depth (d=10 mm), which is close to the radius to the charging coil 126 (about 30 mm). This threshold thus would work as a good determiner of charger-to-IMD alignment, such that if Vy+<Vy+(th), the charging coil 126 would be deemed aligned with the IMD 10, and misaligned if Vy+>Vy+(th). A different threshold could also be stored and applied to determine a more-exacting centered position, such as Vy+(th')=0.14 V, which would define the charging coil 126 as centered when the charging coil 126 is at or below a tighter 20 mm radius with respect to the IMD 10. Depending on the comparison to the one or more magnitude thresholds, the IMD position circuitry 140 may indicate (74, 75) the determined position to the user, such as whether the charging coil 126 is centered, not centered but not misaligned, or misaligned to the user, as explained earlier. As discussed earlier (FIGS. 10A and 10B), more than one sense coil 178 concentric with the charging coil 126 may also be used.

The measured resonant frequency f(res) alone can be also used to determine charger-to-IMD positioning. As shown in FIG. 14B, a resonant frequency threshold f(res)(th)=81.2 kHz establishes a charger-to-IMD radius r of about 27.5 mm at the indicated depth (d=10 mm), which again would work as a good determiner of charger-to-IMD alignment: if f(res) >f(res)(th), the charger coil 126 would be deemed aligned with the IMD 10, and misaligned if f(res)<f(res)(th). A different threshold could again be applied to determine a more-exacting centered position, such as f(res)(th')=81.4 kHz, which would define a tighter 20 mm centering radius, although this additional threshold is not shown in FIG. 14B. Again, the resonant frequency f(res) as measured from more than one sense coil 178 may also be used.

The measured phase angle θ alone can also be used to determine charger-to-IMD positioning. Notice from the data in FIG. 14B that the phase angle θ measured from the sense coil 178 lags the drive signal D significantly (10°) when r=0, and falls off at higher radii, eventually approaching zero degrees nearer to the radius of the charging coil 126 (30 mm). A phase angle threshold θ(th) of about 0.8 degrees again works as a suitable alignment threshold for the geometry of the charging coil 126 in question and at the indicated depth. Again, and although not shown, an additional phase angle threshold could be used to determine centering, and phase angles can be measured from more than one sense coil 178.

Referring again to FIG. 13A, the various thresholds just described (Vy+(th), θ(th), and f(res)(th)) can be stored in database 200 and compared to measured values, as may the three-dimensional data represented in FIG. 14A (Vy(r,d)), θ(r,d), f(res)(r,d)). Additionally, the depth d between the charging coil 126 and the IMD 10, which again may vary from patient to patient, may also be stored. A priori knowledge of depth d may allow the sense coil parameter thresholds to be determined with further accuracy. This can be important, because, as the contours in FIG. 14A show, the measured parameters can vary as a function of IMD 10 depth d, meaning that a single threshold value may not be suitable to determine position (alignment and centering) for all depths.

If the three-dimensional data of FIG. 14A is present, and the depth d is known, an appropriate threshold value for each sense coil parameter can be determined from (e.g., looked up in) database 200. For example, if it is known that the charger-to-IMD depth is 15 mm, and that misalignment should be indicated when the radius r exceeds 31 mm, then a suitable resonant frequency threshold f(res)(th) would be about 80.9 kHz, as shown by the dotted lines in the resonant frequency data of FIG. 14A. Charger-to-IMD depth d may also be calculated or learned and then stored in database 200, allowing appropriate thresholds to be chosen, using for example the technique of U.S. Pat. No. 9,227,075, which technique is not described here.

Variation of measured sense coil parameters with depth notwithstanding, use of phase angle θ to determine charger-to-IMD positioning is particularly promising because of its relative insensitivity to depth d. Referring again to FIG. 14A, note that the contour for the previously chosen threshold θ(th)=0.8 is relatively vertical, particularly at lower depths (d<15 mm). This means that this phase angle threshold θ(th) will work well to determine alignment over a large depth, i.e., from 0<d<15 mm. Within this depth range, the error in the established misalignment radius, e, varies only slightly from about 25-28 mm, which can be tolerable.

Consideration by the IMD position circuitry 140 of more than one measured sense coil parameter can also allow for a determination of both the radius r and depth d between the charging coil 126 and the IMD 10, particularly if the database 200 includes the three-dimensional data of FIG. 14A. Assume for example that module 170 determines the magnitude of Vy, Vy+, to be 0.14 V. As the contour in FIG. 14A demonstrates, it cannot be known whether the charging coil 126 is for example at position X1 or X2 based on Vy+ alone. However, if module 170 further determines that the phase angle θ is 4.0°, then position module 140 can determine (using Vy+(r,d) and θ(r,d)) that the charging coil 126 must be located at position X1, that is at about r=17 mm and d=10 mm relative to IMD 10 (as measured relative to their centers 160 and 150).

In another example, assume that module 170 determines Vy+ to be 0.30 V. As the contour in FIG. 14A demonstrates, it cannot be known whether the charging coil 126 is for example at position Y1 or Y2. However, if module 172 further determines that the resonant frequency is 80.9 kHz, then position module 140 can determine (using Vy+(r,d) and θ(r,d)) that the charging coil 126 must be located at position Y1, that is, at about r=28 and d=18 mm relative to IMD. Consideration of a third measured sense coil parameter (phase angle) can improve position determination accuracy, or verify determined position results.

Because depth d should remain relative constant for a patient, it may not always be strictly necessary for the charging system to compute the depth, especially considering that the depth can be learned using the disclosed technique. For example, consideration of more than sense coil parameter can determine radius r and depth d at different points in time during a charging session (t2; FIG. 12B), or as the patient uses the charging system 100 at different times. The depths at each of these measurement points can be stored in database 200, and should generally not vary. Hence, the determined depth may eventually be averaged from these various measurements, and then simply stored in the database 200 and used without having to determine it each time sense coil measurements are taken.

Knowing where the charging coil 126 is relative to the IMD 10 in terms of both radius r and depth d is useful. As discussed earlier, depth d is usually fixed by the depth at which the IMD 10 is implanted in the patient, because the charging coil assembly 102 is normally pressed against the patient. The patient thus may be unable to do anything to adjust the depth. By contrast, the radius between the charging coil 126 and the IMD 10 is something the patient can adjust by laterally (radially) adjusting the position of the charging coil assembly 102 relative to the IMD 10. Thus, the IMD position circuitry 140 preferably adjusts the threshold (s) per IMD depth. For example, and referring to the f(res) contours in FIG. 14A, if alignment radius is defined as r=32 mm, the alignment threshold for the resonant frequency, f(res)(th), would be set to about 81.4 kHz if the depth is d=5 mm; 81.1 kHz if the depth is d=10 mm; 80.9 kHz if the depth is d=15 mm, etc. The position indicator (e.g., 74) would then only indicate position (in this case misalignment) when f(res) as measured is lower than the depth-appropriate threshold. Similar adjustment of the position thresholds for magnitude Vy+ and phase angle θ based on depth could be similarly determined.

Determination and indication of positioning can also occur by assessment of more than one sense coil parameter, and comparison of more than one threshold. For example, and again referring to the contours of FIG. 14A, misalignment might be indicated if, at depth d=10 mm, f(res)<81.1 kHz and if Vy+>0.23 V, a point indicated as Z at an alignment radius of r=32 mm. The phase angle could also be measured and considered, with misalignment indicated or confirmed if θ<θ(th)=0.1°.

While the alignment and centering algorithm 180 described earlier with respect to FIGS. 12A and 12B focused on use of the magnitude of the voltage of the sense coil (Vy+), it should be noted that the algorithm 180 works equally well the sense coil parameters of phase angle θ or resonant frequency f(res) are used as well. Thus, either of these other sense coil parameters could be measured and compared to appropriate thresholds (steps 194, 202, 208 of algorithm 180) to determine whether the charging coil 126 is centered, aligned but not centered, or misaligned. Further, these same steps may also measure and assess more than one of sense coil parameters Vy+, θ, and f(res), which as just explained can improve the accuracy of the charger-to-IMD position determination.

The sense coil parameters of phase angle θ and resonant frequency f(res) are less affected by the power of the magnetic field 66 provided by the charging coil 126 during the measurement (unlike voltage magnitude Vy+, which would scale with magnetic field power). As such, normalization of these measurements may be unnecessary, and as such it may be unnecessary to use a constant, lower-power test magnetic field during those measurements. In other words, if θ and f(res) are used as the measured sense coil parameters in algorithm 180, the true (possibly varying) magnetic field may be used during the measurements (e.g., during t2), and the test magnetic field can be dispensed with.

One of more of sense coil parameters Vy+, θ, and f(res) can also be used to adjust the power of the magnetic field 66 delivered to the IMD 10. This is useful because non-ideal coupling between the charging coil 126 and the IMD 10 caused by imperfect charger-to-IMD positioning may be remediable by increasing the power of the magnetic field 66 provided to the IMD 10. In other words, if the coupling is low because of charger-to-IMD positioning, the power of the magnetic field is increased to ensure that the IMD 10 receives the same amount of power no matter the coupling.

Power control is discussed further with respect to FIG. 15A, which shows further details concerning power circuitry 145 useable in the charging system. As with position circuitry 140 described earlier, power circuitry 145 can operate as firmware comprising control circuitry 72, although this is not strictly necessary as analog circuitry can be used for certain aspects as well. Control circuitry 72 may again contain Vy magnitude and phase angle determination module 170, resonant frequency determination module 172, and database 200, and in FIG. 15A those modules have been moved out from position circuitry 140 and instead are common to (provide data to) both of position circuitry 140 and power circuitry 145.

In one example, data regarding the position of the charging coil 126 with respect to the IMD 10—at least the radius r, and preferably also depth d—is provided to power circuitry 145. As explained earlier (FIG. 14A), both r and d can be determined by assessing two or more of the sense coil parameters of Vy+, θ, and f(res). However, and also as earlier explained, depth d can be programmed into the control circuitry 72 and/or learned.

Power circuitry 145 can assess radius r and depth d to determine an appropriate power for the magnetic field 66. As explained earlier, magnetic field power can set by setting the duty cycle DC of the drive signal D, because increasing the duty cycle DC will increase Icharge flowing through the charging coil 126. However, increasing drive signal duty cycle is merely one way of increasing magnetic field power and other ways can also be used, depending on the charging circuitry 64 that is used to energize the charging coil 126.

A look up table 146 may be stored in a memory within or accessible to the power circuitry 145, which is used to set a duty cycle DC for the square wave generator 65 and the charging circuitry 64 depending on the radius and depth of the charging coil 126 relative to the IMD 10. For example, if the radius and depth are both relatively small (r1, d1), the charging coil 126 and IMD 10 would be relatively well coupled. Thus, more of the magnetic field 66 generated at the charging coil 126 would reach the IMD 10, and as a result the duty cycle can be relatively small (DC1) for this position. By contrast, if either or both of the radius and depth are larger (e.g., r2, d2), coupling would be poorer. Thus, power circuitry 145 would direct the square wave generator 65 to increase the duty cycle (e.g., to DC3) to ensure that the IMD 10 is receiving an adequate amount of power. As noted above, it is preferable that the IMD 10 receive a constant amount of power, regardless of charger-to-IMD positioning.

Determining the amount of power the IMD 10 receives can be experimentally determined in various manners by measure various parameters in the IMD 10. In one example, the received power can be assessed as the amount of charging current, Ibat (FIG. 15A), the IMD 10's battery 14 receives. One skilled will appreciate that as coupling drops (i.e., as r or d increases), Ibat would also drop if magnetic field power were not adjusted. This is shown in FIG. 15B, which shows the power that IMD 10 receives (Ibat) as a function of radius and depth when the charging coil 126 produces a magnetic field 66 of a constant power (i.e., when Icharge and duty cycle DC are constant). Specifically, FIG. 15B shows various regions for Ibat as derived from experimentation. As shown, lower values for Ibat (e.g., between Ibat1 and Ibat2) are associated with poor coupling, and a position region having higher values for radius r and/or depth d. To compensate, this position region is provided with a high duty cycle (DC5), and thus a higher magnetic field power, in look up table 146. By contrast, higher values for Ibat (e.g., >Ibat5) are associated with high coupling, and a position region having lower values for radius r and/or depth d. To compensate, this position region is provided with a low duty cycle (DC1), and thus a lower magnetic field power, in look up table 146. Preferably the duty cycle associated with each position region will cause Ibat in the IMD 10 to be relatively constant, and hence independent of charger-to-IMD position. Alternatively, the duty cycle chosen (power) may not render a constant Ibat for all potential positions of the charging coil 126 relative to the IMD 10, but will at least result in a value for Ibat that doesn't drop below a minimum value, thus ensuring that the IMD 10 receives an adequate amount of power regardless of charger-to-IMD position.

While it is preferred that the power circuitry 145 determine an appropriate adjustments to the power of magnetic field 66 using knowledge of both radius and depth (as determined using sense coil parameters Vy+, θ, and/or f(res)), this is not strictly necessary. Instead, power circuitry 145 may instead receive the sense coil parameters Vy+, θ, and/or f(res) themselves and adjust the power, without determining radius and depth as an intermediate step.

In one example, adjustment to the power of the magnetic field 66 occurs using sense coil measurements taken during the issuance of test or default magnetic field from the charging coil 126, as was discussed earlier in conjunction with FIG. 12B. In this example, one or more of sense coil parameters Vy+, θ, and/or f(res) are periodically measured during the test magnetic field (e.g., during times t1)—and with the calculated power (e.g., duty cycle DC) used during the subsequent true magnetic field period (t2). In this way, adjustments to magnetic field power are made every 30 seconds or so using the examples for t1 and t2 provided earlier, which reasonably accommodates the time scale that the charging coil assembly 102 would be expected to move. Of course, this is not strictly necessary. Further, although not shown in FIG. 12B, additional sense coil parameters measurements could be taken (during time periods t2) specifically for the purpose of magnetic field power adjustment. Thus, there can be different time periods at which sense coil parameters measurements are taken for the purpose of determining charger-to-IMD positioning, and for the purpose of magnetic field power adjustment.

Similar to what was discussed earlier in conjunction with FIG. 12B, sense coil parameter measurements for the purpose of magnetic field power adjustment need not be taken using the low-powered test magnetic field, but could simply use the true magnetic field operative to charge the IMD 10. As was discussed earlier, this may make normalizing the measurements to the current power of the magnetic field more important, particularly the voltage magnitude Vy+ measurements, but less so for the phase angle θ and the resonant frequency f(res) measurements.

Adjustment of the power of the magnetic field using power circuitry 145 can also occur as a function of the determined charger-to-IMD position. For example, power circuitry 145 may only be enabled to adjust the power if the position circuitry 140 determines that the charging coil 126 is aligned with the IMD 10. In this regard, and as shown in FIG. 15A, position circuitry 140 may communicate the status of alignment via signal 147 to the power circuitry 145.

The inventors realize further that it is beneficial during the provision of power to the IMD 10 to provide a true magnetic field 66 that is optimized at the resonant frequency of the charger/IMD system—that is, a magnetic field optimized in frequency given the mutual inductance provided by the coupled charger/IMD system. Providing power at the resonant frequency means that more of the power of the magnetic field 66 will reach the IMD 10 and thus used to charge the IMD 10's battery 14. Further, providing power at the resonant frequency increases the signal induced on the sense coil (Vy), thus making it easier to deduce magnitude Vy+, phase angle θ, and resonant frequency f(res). Note that this use of resonant frequency is different from the purpose described earlier: while f(res) can be measured during test periods (t2) and used to determine charger to IMD positioning and/or how to adjust magnetic field power (e.g., by duty cycle adjustment), here we refer to adjustment of the frequency of the magnetic field 66 during the provision of a true magnetic field.

Fortunately, providing power during a true magnetic field can use the same circuitry described earlier to measure f(res) as useful for position determinations and power adjustment. For example, during a measurement period (t2; see FIG. 12B), it may be determined that the resonant frequency of the charger/IMD system is f(res). As described earlier, this f(res) measurement can be used to determine and indicate (74, 75) IMD-to-charger position, and to adjust the power of the subsequent true magnetic field (t1), for example, by varying the duty cycle DC of the drive signal D applied to charging circuitry 64.

Further, the frequency of the drive signal may independently be set to (or allowed to continue to remain at) f(res) for the subsequent true magnetic field period (t1) to ensure efficiency delivery of power to the IMD 10. Notice that this adjustment to the frequency of the magnetic field 66 can be independent of adjustment to its power. As described earlier, the drive signal D has a duty cycle (power) equal to a/a+b, while its frequency is 1/a+b. Thus, while f(res) is governed by a+b, 'a' can still be varied independently within the period of the drive signal to set the duty cycle DC.

As with power adjustment, it may be reasonable to measure f(res) during test periods (t2), and to set f=f(res) during the subsequent during the subsequent true magnetic field period (t2). In this way, adjustments to the frequency to match the resonance of the charger/IMD system are made every 30 seconds or so (for example). However, the frequency of the drive signal D—and hence the frequency of the magnetic field—could also be adjusted on a different time scale, or adjusted pseudo continuously by continuously sampling sense coil voltage (and determining f(res) during production of the true magnetic field.

Figure 2:
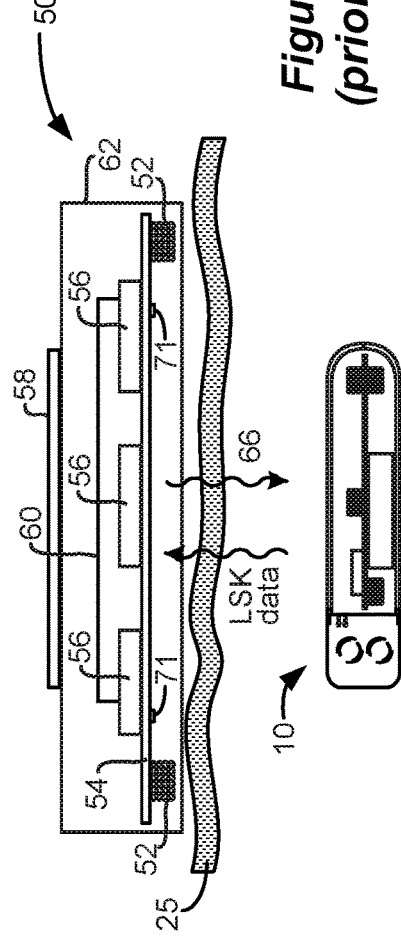

While the disclosed IMD position and power adjustment techniques are described in the context of a charger system 100 having a separate electronics module 104 and charging coil assembly 102 (see FIGS. 5A and 5B), this is not necessary. Instead, the described techniques can also be implemented in an integrated external charger in which electronics, charging coil, and one or more sense coils are housed together. For example, FIG. 16 shows such an integrated external charger 50' with all components housed in a single housing 62, which is generally similar to that described earlier in FIG. 2. Charger 50' includes a circuit board 54 that carries a primary charging coil 52 winding. The traces of the circuit board 54 can include one or more sense coils 178 formed in any of the various manners described. Control circuitry 72' can be programmed with position circuitry 140, power circuitry 145, and other supporting circuitry and programs, all of which were explained in detail above. Thus, it is not important to the disclosed technique that the charging/sense coils be separate from the electronics, or that they be housed in separate housings.

To this point, the disclosed sense coils can deduce charger-to-IMD position (e.g., centered and/or aligned), but lack the ability to deduce a direction by which the charging coil assembly 102 may be non-centered or misaligned. Nonetheless, the sense coils in charging system 100 can be modified to provide an indication to the patient a direction of misalignment or a non-centered condition.

Figure 17B:
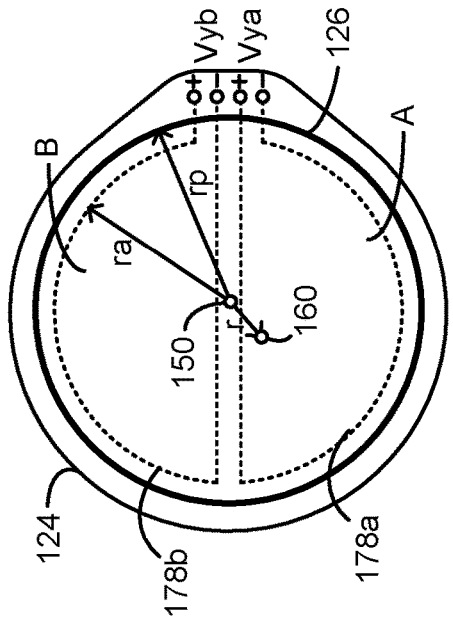
Figure 17D:
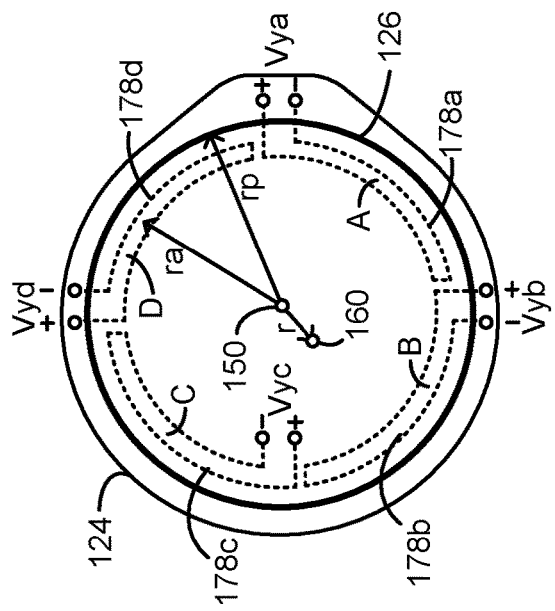
Figure 17A:
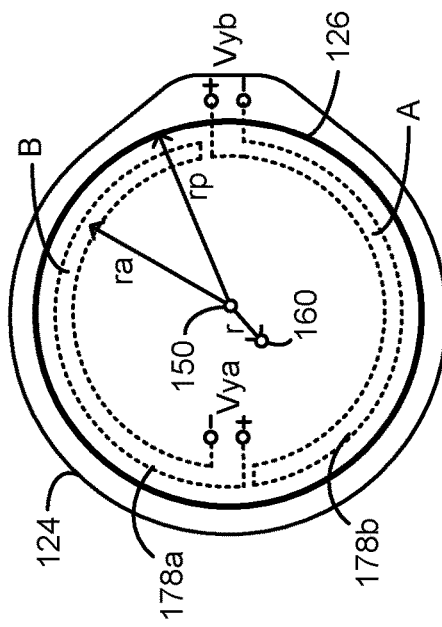

For example, FIG. 17A includes two alignment sense coils 178*a* and 178*b* across which voltages Vya and Vyb can be induced. In the example shown, the alignment sense coils 178*a* and 178*b* comprise edge detection coils of the type disclosed earlier with respect to FIGS. 7A-7C, but this is not strictly necessary. Further, the two illustrated coils 178*a* and 178*b* could operate as centering sense coils, like coils 129 of FIGS. 9A-9C, or as combined alignment/centering sense coils, like coils 130 of FIGS. 11A and 11B. Further, a pair of alignment sense coils and a pair of centering sense coils could be used, similar to that shown in FIGS. 10A and 10B. These alternatives aren't illustrated for simplicity.

It is seen in FIG. 17A that sense coils 178*a* and 178*b* each cover roughly half of the circumference of the PCB 124, as shown by areas A and B. If the charging coil assembly 102 (charging coil 126) shifts such that the IMD 10 (not shown) eclipses area A of sense coils 178*a*, then the magnitude Vya+ will drop. The control circuitry 72 in the electronics module 104 would thus understand that the charging coil assembly 102 should be moved downwards to be in better alignment (or better centered) with the IMD 10. Likewise, if the IMD 10 eclipses area B of sense coil 178*b*, then magnitude Vyb+ will drop, indicating that the charging coil assembly 102 should be moved upwards. The direction of misalignment or non-centered, or more preferably the direction of movement necessary to fix alignment or centering, can be indicated by the electronics modules user interface, and U.S. Pat. No. 8,473,066 discusses various means of indication, including direction-indicating LEDs that can be illuminated on the housing 105. The sense coil parameters of phase angle θ and resonant frequency f(res) could also be measured from each of sense coils 178*a* and 178*b* to assist determining directional charger-to-IMD positioning, and magnetic field power adjustment.

FIG. 17B is similar to FIG. 17A, but increases the areas A and B encompassed by alignment (or sense) coils 178*a* and 178*b*, with each coil essentially covering a semicircle. In this example, induced voltages Vya and Vyb can both be used to determine a misalignment or non-centered direction. For example, if Vya+ drops relatively far in value from its maximum value, while Vyb+ only drops a small amount, that would indicate that the IMD 10 is eclipsing are A to a great extent, but eclipsing area B to only a small extent. Thus, the charging system 100 could indicate in this example that the charging coil assembly should be moved upward to better align or center the assembly with the IMD. Again, phase angle θ and resonant frequency f(res) could also be measured from each of sense coils 178*a* and 178*b* in FIG. 14B, and used for magnetic field power adjustment. Note that due to the non-arcuate nature of areas A and B encompassed by the sense coils 178*a* and 178*b*, and unlike earlier examples of sense coils, sense coils 178*a* and 178*b* are not concentric with the charging coil 126.

Figure 17C:
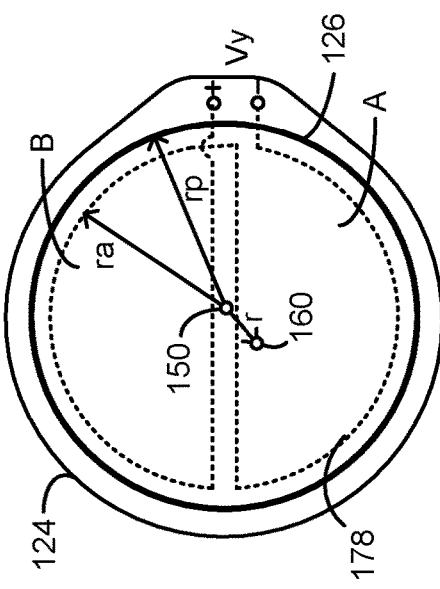

FIG. 17C is similar to FIG. 17B, but connects the two sense coils together to form a single differential sense coil 178, sometimes referred to as a butterfly coil. In this instance, the direction of misalignment or non-centering would be indicated by the relative polarity of induced voltage Vy. If Vy is significantly negative, the IMD 10 would largely be eclipsing area A, while if Vy is significantly positive, it would largely be eclipsing area B. If Vy=0, this would indicate that the charging coil 126 and IMD 10 are perfectly aligned. Phase angle θ and resonant frequency f(res) can also be measured from sense coil 178 in FIG. 14C, with phase angle being particularly useful in determining the polarity of Vy. Sense coil 178 is also not concentric with the charger coil 126.

FIG. 17D includes sense coils 178a-d that are similar to those in FIG. 17A, but there are more than two, with each covering roughly a quarter of the circumference of the circuit board 124, as shown by areas A-D. This provides directionality information along orthogonal axes (along X and Y directions), thus allowing the charging system to not only determine whether the charging coil 126 is misaligned or not centered in the up/down direction, but in a left/right direction as well.

Figure 17E:
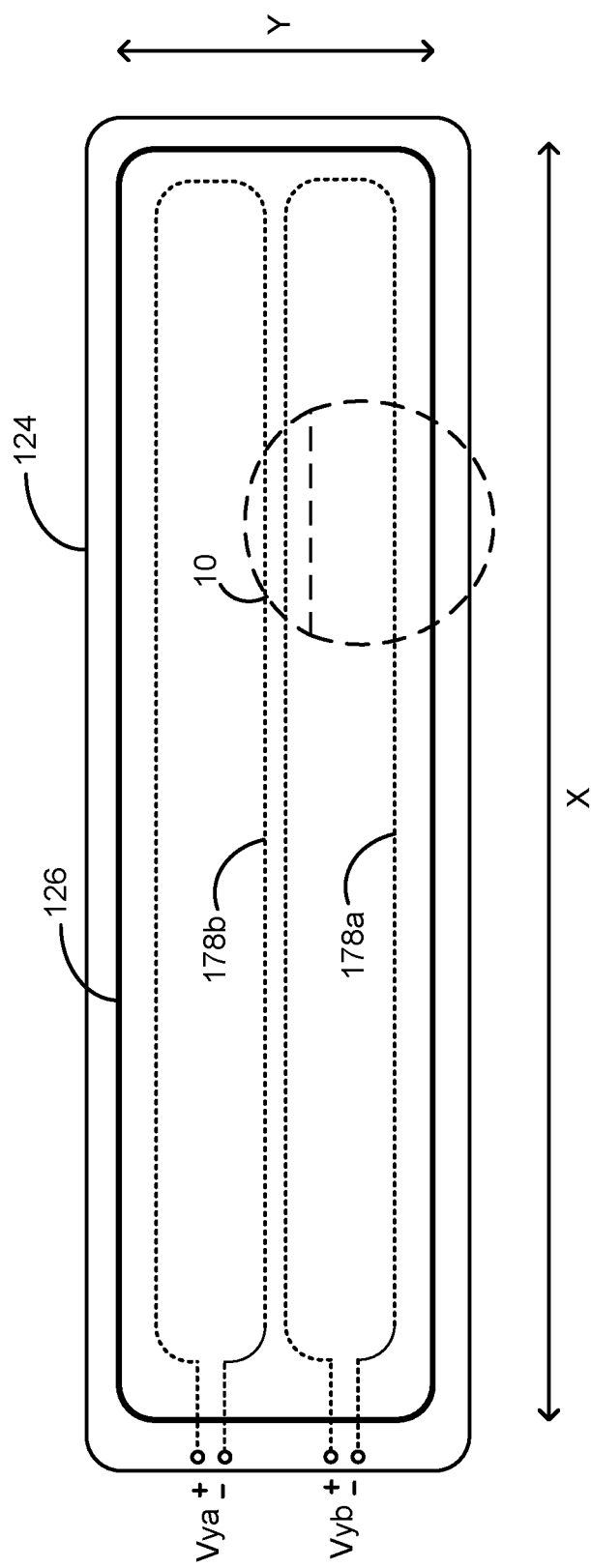

FIG. 17E shows another example in which sense coils can be used in charging system 100 to deduce a direction of misalignment or a non-centered condition. In FIG. 17E, the charging coil 126 is generally elongated (more specifically, rectangular in shape as shown), and has a long dimension X that is significantly longer than its other orthogonal dimension Y. Also included within the charging coil 128 (e.g., within PCB 124) are sense coils 178a and 178b, which likewise have a long X dimension and a significantly shorter Y dimension. Two sense coils are shown, but there could be three or more. Dimension X is preferably significantly larger than the IMD 10. As a result, alignment between the charging coil 126 and the IMD 10 in the X direction is generally not of concern, as it would be expected that the IMD 10 would be well within the X dimension. However, alignment in the smaller Y direction could still be of concern, and so sense coils 178a and 178b are used to determine misalignment in the Y direction, which can be accomplished by monitoring Vya and Vyb as explained above. Again, any one or more of magnitude, phase angle, and/or resonant frequency could be gleaned from Vya and/or Vyb to assist in determining alignment in the Y direction. The sense coils 178a and 178b, although separate as in FIG. 17B, can also be connected together to form a single sense coil as in FIG. 17C if desired. Note that a charging coil 126 and sense coils 178 of the shape shown in FIG. 17E can be used in a generally linear-shaped charging system, such as that used with or in a charging belt, as mentioned earlier. Using such a charging belt, a patient would generally not have to worry around alignment of the belt around his waist (X; in an SCS application), but would instead only need to worry about adjusting the belt higher or lower on his waist (Y).

To this point, what has been assessed from the various disclosed sense coils has been a Voltage (e.g., Va, Vc, Vx, Vy). However, sense coil current could be assessed as well, with current magnitude, phase, or resonance being used in the disclosed alignment and power adjustment techniques.

Still other variations are possible to charging system 100. FIG. 18 for example shows that the one or more sense coils 178 in the charging coil assembly 102 need not merely be passive devices to sense magnetic fields, may also be actively energized to produce their own magnetic fields to assist with alignment and/or power adjustment. As shown, sense coil drive circuitry 65 has been added to the electronics module 104, which in this example produces an AC current, Isense, driven to sense coil 178. Any of the sense coils disclosed earlier could be used in this example. The frequency of Isense may equal the resonant frequency at which the charging coil 126 is driven, although this isn't strictly necessary. The frequency of Isense may be tuned in accordance with a capacitor 131 coupled to the sense coil. This capacitor 131 is shown in parallel with the sense coil, but could also be placed in series.

The one or more sense coils 178 may be driven with Isense during periods when the charging coil 126 is also being driven with Icharge, but preferably would be driven during short testing periods (t2) when charging coil 126 is not energized (t1) (see FIG. 12B). As sense coil is driven, a magnetic field 67 is formed. A voltage Vsense will build up across the sense coil 178, which voltage as before will be affected by coupling to both the charging coil 126 and the position of the IMD 10 relative to the sense coil. As before, Vsense will be smaller if the IMD 10 is bounded by the sense coil 178, and larger if the IMD is not bounded by the sense coil. Thus, Vsense may again be compared to one or more threshold to determine alignment, centering, and/or presence of the IMD 10, and may additionally be used to adjust the power of the magnetic field 66 generated by the charging coil 126, consistent with the principles explained earlier.

FIG. 19 show another variation of charging system 100 in which telemetered feedback from the IMD 10 is used to assist with charger-to-IMD positioning and/or magnetic field power adjustment. In this example, a parameter indicative of the coupling between the primary charging coil 126 in the charging coil assembly 102 and the secondary charging coil 36 in the IMD 10 is telemetered to the charging system 100. In one example, the coupling parameter comprises the current, Ibat, flowing into the battery during charging, which parameter can generally scale with the extent to which the secondary charging coil 36 is receiving the primary charging coil 126's magnetic field 66. This coupling parameter however is merely one example, and other parameters measured in the IMD 10 could be used as well, such as the DC voltage produced by rectifier 38.

The battery charging current Ibat can be measured by circuitry 41 in the IMD 10 in conventional fashion. For example, although not shown, Ibat can be flow through a small sense resistor (e.g., R=1 ohm) and the voltage across that resistor (V) measured by a differential amplifier, thus allowing the current to be deduced (Ibat=V/R). Ibat (or the coupling parameter more generally) is received at the IMD 10's control circuitry 42, and can then be telemetered to the charging system 100. Such telemetry can occur in a number of ways. For example, the coupling parameter can be modulated as LSK data, where it affects Vcoil produced by the charging coil 126. Vcoil can then be demodulated (68) as explained earlier, thus informing the charging system 100's control circuitry 72 of the value of the telemetered coupling parameter.

Alternatively, the coupling parameter can be telemetered via another communication link established between an antenna 45 in the IMD 10 and an antenna 127 in the charging coil assembly 102. Antenna 45 may comprise an antenna otherwise used in the IMD 10 to communicate with an external device such as a hand-held external controller or a clinician's programmer, which external devices are explained in further detail in U.S. Patent Application Publication 2015/0360038. Antennas 45 and 127 may comprise coils which communicate via near-field magnetic induction using an appropriate modulation scheme, such as Frequency Shift Keying (FSK). Antennas 45 and 127 may also comprise short-range RF antennas that communicate via far-field electromagnetic waves in accordance with a communication standard such as Bluetooth, WiFi, MICS, Zigbee or other standards. When a discrete antenna 127 is used in the charging coil assembly 102 to receive the coupling parameter, the received data (represented as voltage Vtelem) can be reported through the cable 106 to the control circuitry 72 in the electronics module 104, which control circuitry can then demodulate the data. Demodulation circuitry for the antenna 127 could also be located in the charging coil assembly 102.

Receipt of the coupling parameter at the control circuitry 72 (Vtelem) in conjunction with data reported from the one or more sense coils (Vsense) can improve the disclosed charger-to-IMD position determination, and/or magnetic field power adjustment. For example, Vy might indicate that the charging coil 126 is misaligned with the IMD 10 (because Vy>Vy(th)). However, if the coupling parameter indicates that the battery 14 in the IMD 10 is receive an adequate amount of current (Ibat), position circuitry 140 may ultimately determine that alignment is proper. Further, if Ibat is sufficient, power circuitry 145 may decide to not increase the power of the magnetic field 66 (e.g., the duty cycle (DC) described earlier), or may increase the power to a lesser degree than may otherwise be indicated by look up table 146 (FIG. 15A).

While the disclosed techniques are described in the context of a charger system 100 that is used to charge a battery 14 in an IMD 10, this is not strictly necessary. Charger system 100 can also be used to provide continuous magnetic field 66 power to an IMD that lacks a battery. Charger-to-IMD positioning and power adjustment are important in this context as well, and perhaps even more so because an IMD lacking a battery may cease operating if it does not receive adequate power from a poorly positioned or non-power-optimized external charger.

Referring to "a" structure in the attached claims should be construed as covering one or more of the structure, not just a single structure.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover equivalents that may fall within the spirit and scope of the present invention as defined by the claims.

What is claimed is:

1. An external charger for wirelessly providing energy to an implantable medical device (IMD), comprising:
   a charging coil configured when energized by a drive signal to produce a magnetic field to wirelessly provide energy to the IMD as a coupled system;
   a sense coil, wherein the sense coil is configured to be induced by the magnetic field with an induced signal affected by a position of the charging coil with respect to the IMD; and
   control circuitry configured to determine a plurality of parameters using the induced signal, wherein the control circuitry is further configured to determine using the plurality of parameters the position of the charging coil with respect to the IMD.

2. The external charger of claim 1, wherein the sense coil is concentric with the charging coil.

3. The external charger of claim 1, further comprising a user interface configured to indicate the determined positions to a user.

4. The external charger of claim 1, wherein the plurality of parameters comprise a plurality including at least one of:
   a magnitude of the induced signal,
   a phase angle between the induced signal and the drive signal, and
   a resonant frequency of the coupled system.

5. The external charger of claim 1,
   wherein the control circuitry is configured to determine from the plurality of parameters whether the charging coil is aligned, centered, or aligned and centered with respect to the IMD,
   wherein centered comprises a condition in which the coupling between the charging coil and the IMD is higher than a first coupling value, and
   wherein aligned comprises a condition in which the coupling between the charging coil and the IMD is higher than a second coupling value lower than the first coupling value.

6. The external charger of claim 1, further comprising an electronics module and a charging coil assembly coupled to the electronics module by a cable,
   wherein the charging coil and the sense coil are within the charging coil assembly, and
   wherein the control circuitry is within the electronics module.

7. The external charger of claim 1, further comprising a circuit board, wherein the sense coil is formed in one or more traces in the circuit board.

8. The external charger of claim 7, wherein the charging coil comprises a wire winding placed on a side of the circuit board.

9. The external charger of claim 7, wherein the charging coil comprises a wire winding, and wherein the circuit board is placed within the wire winding of the charging coil.

10. The external charger of claim 1, wherein the control circuitry further comprises or has access to a database, wherein the database comprises a plurality of thresholds, wherein the control circuitry is configured to compare each of the plurality of parameters to one of the thresholds to determine the position of the charging coil with respect to the IMD.

11. The external charger of claim 1, wherein the control circuitry is configured to determine a radius at which the charging coil is laterally offset with respect to the IMD.

12. The external charger of claim 11, wherein the control circuit is further configured to determine a depth between the charging coil and the IMD.

13. The external charger of claim 1, wherein the control circuitry further comprises or has access to a database, wherein the database comprises values for the plurality of parameters at different radial offsets and depths between the charging coil and the IMD, wherein the control circuitry is configured to compare the plurality of parameters to the values to determine the position of the charging coil with respect to the IMD.

14. The external charger of claim 1, wherein the determined position comprises a radius and depth between the charging coil and the IMD.

15. The external charger of claim 1, wherein the sense coil comprises a circle.

16. The external charger of claim 1, wherein the sense coil comprises two circles of different radii.

17. The external charger of claim 16, wherein the two circles are connected such that such that a current flowing through the two circles will flow in different directions in the two circles.

* * * * *